US012723044B2

(12) United States Patent
Wan et al.

(10) Patent No.: US 12,723,044 B2
(45) Date of Patent: Sep. 1, 2026

(54) HETEROCYCLIC SUBSTITUTED FUSED γ-CARBOLINE DERIVATIVE, PREPARATION METHOD THEREFOR, INTERMEDIATE THEREOF AND USE THEREOF

(71) Applicants: SHUJING BIOPHARMA CO., LTD, Shanghai (CN); JIANGSU NHWA PHARMACEUTICAL CO., LTD, Xuzhou (CN)

(72) Inventors: Zehong Wan, Shanghai (CN); Jiaquan Feng, Shanghai (CN); Yongqi Wu, Shanghai (CN); Jun Qin, Shanghai (CN); Bingcheng Zhou, Shanghai (CN); Zhijing Hu, Shanghai (CN); Xinjian Jiang, Shanghai (CN); Zijin Feng, Shanghai (CN)

(73) Assignees: SHUJING BIOPHARMA CO., LTD, Shanghai (CN); JIANGSU NHWA PHARMACEUTICAL CO., LTD, Xuzhou (CN)

( * ) Notice: Subject to any disclaimer, the term of this patent is extended or adjusted under 35 U.S.C. 154(b) by 684 days.

(21) Appl. No.: 18/027,226

(22) PCT Filed: Oct. 8, 2021

(86) PCT No.: PCT/CN2021/122546

§ 371 (c)(1),
(2) Date: Mar. 20, 2023

(87) PCT Pub. No.: WO2022/073470

PCT Pub. Date: Apr. 14, 2022

(65) Prior Publication Data

US 2023/0339949 A1 Oct. 26, 2023

(30) Foreign Application Priority Data

Oct. 9, 2020 (CN) ......................... 202011074344.9
Oct. 9, 2020 (CN) ......................... 202011075840.6

(51) Int. Cl.
*C07D 471/14* (2006.01)
*A61P 25/18* (2006.01)

(52) U.S. Cl.
CPC ............ *C07D 471/14* (2013.01); *A61P 25/18* (2018.01)

(58) Field of Classification Search
CPC ................ C07D 471/14; C07D 471/16; A61K 31/4965; A61K 31/4985
See application file for complete search history.

(56) References Cited

U.S. PATENT DOCUMENTS

2017/0319580 A1 11/2017 Yao et al.
2019/0192511 A1 6/2019 Li

FOREIGN PATENT DOCUMENTS

| | | | |
|---|---|---|---|
| CN | 103619841 | A | 3/2014 |
| CN | 105168219 | A | 12/2015 |
| CN | 106535898 | A | 3/2017 |
| CN | 110430879 | A | 11/2019 |
| EP | 0905136 | A1 | 3/1999 |
| JP | 2005501092 | A | 1/2005 |
| WO | WO-0077002 | A1 | 12/2000 |
| WO | WO-03014125 | A1 | 2/2003 |
| WO | WO-2009145900 | A1 | 12/2009 |
| WO | 2012096929 | A2 | 7/2012 |
| WO | WO-2015154025 | A1 | 10/2015 |
| WO | WO-2017117514 | A1 | 7/2017 |
| WO | WO-2017132408 | A1 | 8/2017 |
| WO | WO-2018175969 | A1 | 9/2018 |

OTHER PUBLICATIONS

Oct. 9, 2024 First Office Action issued in Chinese Patent Application No. 2021800683567.
Sep. 20, 2024 Chinese Search Report issued in Chinese Patent Application No. 2021800683567.
Feb. 28, 2025 Notice of Preliminary Rejection issued in Korean Patent Application No. 10-2023-7009354.
Nov. 11, 2025 Preliminary Office Action issued in Brazil Patent Application No. 1120240141330.
Si, T et al., Advance on role of 5-HT1A receptor in psychopathology of mental disorders and potential therapeutic effects of 5-HT1A receptor partial agonist, Chin J New Drugs Clin Rem, 2018, 37, 503-508 (Dec. 31, 2018).
Jan. 6, 2022 International Search Report issued in International Patent Application No. PCT/CN2021/122546.
Jan. 6, 2022 Written Opinion of the International Searching Authority issued in International Patent Application No. PCT/CN2021/122546.

(Continued)

*Primary Examiner* — Sahar Javanmard
(74) *Attorney, Agent, or Firm* — Harness, Dickey & Pierce, P.L.C.

(57) ABSTRACT

The present invention relates to a heterocyclic substituted fused γ-carboline derivative, a preparation method therefor, an intermediate thereof and use thereof. The heterocyclic substituted fused γ-carboline derivative has a compound structure as represented by formula (I). Such compound can be used for preparing a medicament for treating neuropsychiatric diseases.

(I)

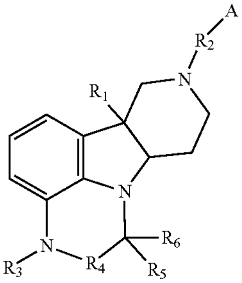

13 Claims, No Drawings

(56) References Cited

OTHER PUBLICATIONS

Aug. 22, 2022 Taiwan Office Action issued in Taiwan Patent Application No. 111102580.

Li, Peng et al., "Discovery of a tetracyclic quinoxaline derivative as a potent and orally active multifunctional drug candidate for the treatment of neuropsychiatric and neurological disorders", Journal of medicinal chemistry, vol. 57, No. 6, Feb. 21, 2014, pp. 2670-2682.

Aug. 30, 2023 Australian Office Action issued in Australian Patent Application No. AU2021356875.

Jan. 29, 2024 European Search Report issued in European Patent Application No. 21876988.3.

Apr. 2, 2024 First Office Action issued in Japanese Patent Application No. 2023-546376.

Jun. 20, 2024 First Office Action issued in Canadian Patent Application No. 3194682.

HETEROCYCLIC SUBSTITUTED FUSED γ-CARBOLINE DERIVATIVE, PREPARATION METHOD THEREFOR, INTERMEDIATE THEREOF AND USE THEREOF

CROSS-REFERENCE TO RELATED APPLICATIONS

The present application is a U.S. National Phase Application under 35 U.S.C. 371 of International Application No. PCT/CN2021/122546, filed on Oct. 8, 2021, which claims the priority of Chinese patent application 202011075840.6 filed on Oct. 9, 2020 and claims the priority of Chinese patent application 202011074344.9 filed on Oct. 9, 2020. The contents of the Chinese patent applications are incorporated herein by reference in their entireties.

TECHNICAL FIELD

The present disclosure belongs to the field of medicinal chemistry and specifically relates to a heterocyclic substituted fused γ-carboline derivative, a synthesis thereof and a use thereof. More specifically, the present disclosure relates to the heterocyclic substituted fused γ-carboline derivative, a preparation method therefor, an intermediate thereof, a pharmaceutical composition comprising the heterocyclic substituted fused γ-carboline derivative, and a use of the heterocyclic substituted fused γ-carboline derivative and the pharmaceutical composition thereof in the manufacture of a medicament for preventing and/or treating a neuropsychiatric disease.

BACKGROUND

Schizophrenia is a disease characterized by deep division of cognition and emotion, which shows that the most basic human behaviors are affected, such as language, thought, perception and self-perception. The symptoms of the disease cover a wide range, and the most common symptoms are psychiatric disorders, such as hallucinations, delusions and illusions.

Approximately 1% of people worldwide suffer from schizophrenia, and only 5% of all patients treated can eventually recover completely. In addition, schizophrenia usually triggers comorbidities such as anxiety disorder, depression, or psychotropic drug abuse.

Traditionally, antipsychotics that exert pharmacological effects by blocking dopamine D2 receptor are called the first generation antipsychotics, that is, "typical" antipsychotics (such as haloperidol). They have a breakthrough in treating positive symptoms of schizophrenia, but fail to treat negative symptoms and cognitive impairment. Typical antipsychotics generally have severe EPS side effects and are ineffective in one-third of patients with schizophrenia.

Since the 1960s, a series of new generation antipsychotics were developed, including Ziprasidone, Risperidone, etc., and the new generation antipsychotics are called the second generation antipsychotics, that is, new antipsychotics. Although their respective pharmacological effects are not completely consistent, they share the same pharmacological characteristics, namely, their affinity for 5-hydroxytryptamine (5-HT) receptor (5-HT1A, 2A, 2c) and noradrenergic (NA) receptor (α1, α2) is much higher than those for D2 receptor, resulting in a higher D2/5-HT2A ratio. Compared with the first generation antipsychotics, clinical effects of the second generation antipsychotics have more advantages. They are not only as effective as traditional antipsychotics for positive symptoms, but also effective for negative symptoms and cognitive deficit symptoms, and have a broader spectrum of action. However, these drugs have adverse effects such as QT gap prolongation, hyperprolactinemia, and weight gain. Therefore, the search for drugs that can be effective against positive, negative symptoms and cognitive impairment in schizophrenia with few side effects is now a hot topic of research.

The 5-hydroxytryptamine system plays an important role in regulating the function of prefrontal cortex (PFC), including emotional control, cognitive behavior and working memory. PFC pyramidal neurons and GABA interneurons contain several 5-hydroxytryptamine receptor subtypes, such as 5-HT1A and 5-HT2A with particularly high density. Recently, it has been proved that PFC and NMDA receptor channels are the targets of 5-HT1AR. These two receptors regulate excitatory neurons in cerebral cortex, thus affecting cognitive function. Indeed, various preclinical data indicate that 5-HT1AR may be a new target for developing antipsychotic drugs. The high affinity of atypical antipsychotics (such as olanzapine, aripiprazole) for 5-HT1AR and its low EPS side effects all indicate that the 5-hydroxytryptamine system plays an important role in regulating the function of prefrontal cortex (PFC), including emotional control, cognitive behavior and working memory. PFC pyramidal neurons and GABA interneurons contain several 5-hydroxytryptamine receptor subtypes, such as 5-HT1A and 5-HT2A with particularly high density. Recent studies have shown that 5-HT1A agonists are associated with atypical antipsychotic treatment and can improve negative symptoms and cognitive impairment. In the treatment of schizophrenia with clozapine, an atypical antipsychotic drug, it has been found that 5-HT2A plays an important role, involving all aspects of perception, emotional regulation and motor control. Blocking 5-HT2A receptor normalizes the release of dopamine and play an antipsychotic role. In addition, 5-HT2C receptors are closely associated with weight gain.

The distribution of D3 receptor in the brain is mainly selectively distributed in the limbic system. There are two main DA neural pathways in the brain, one is a substantia nigra striatum pathway which regulates motor function; the other is a DA pathway in the prefrontal cortex of the ventral tegmental area of the midbrain, which is closely related to learning cognition and emotional activities, and its abnormal function will lead to schizophrenia. The DA pathway is also the main pathway for reward effects in the brain. D3R is distributed in both DA neural pathways and has complex interactions with other DA receptor subtypes, and may be a target for antipsychotic treatment. Antagonism of selective D3 receptor can reduce the negative and cognitive symptoms of schizophrenia, in addition, it can prevent extrapyramidal side effects, including tardive dyskinesia and Parkinson's disease. Therefore, it is of great significance for clinical treatment to find an anti-schizophrenia drug of multi-receptor binding with low side effects.

In 2019, FDA newly approved an anti-schizophrenia drug Lumateperone (R&D code ITI-007), which acts as an antagonist of 5-HT2A receptor and antagonizes several dopamine receptor subtypes (D1, D2 and D4). Lumateperone has moderate inhibitory effect on 5-HT transporter reuptake. Lumateperone has an additional off-target antagonistic effect on α-1 receptor and has no obvious antimuscarinic or antihistaminergic properties, and its specific structure is as follows:

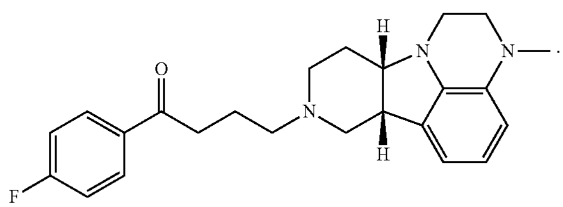 [SMILES: CN1CCN2c3c(cccc31)[C@@H]1CN(CCCC(=O)c3ccc(F)cc3)CC[C@@H]12]

Patent PCT/US2017/015178 discloses a compound of Markush general formula, which acts on receptors such as 5-HT2A, D2, D1 and SERT (serotonin reuptake transporter) and has potential therapeutic activities for schizophrenia and Parkinson's disease,

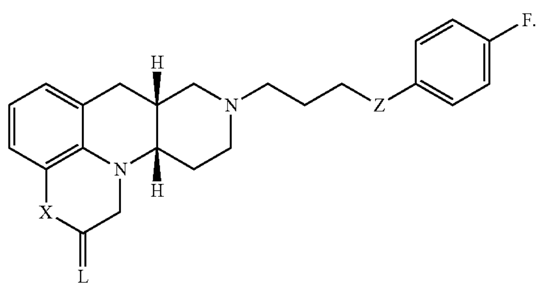

Although there are many therapeutic drugs used for anti-schizophrenia, there are still many kinds of adverse reactions in the current clinical use of schizophrenia drugs. For example, among the patients taking aripiprazole, a widely used atypical anti-schizophrenia drug, more than 10% of the patients will experience adverse reactions including weight gain, headache, akathisia, insomnia and gastrointestinal discomfort, which causes patients to discontinue their medication and make the disease recur. In addition, although current anti-schizophrenia negative symptoms (referring to the defects of normal emotional reaction and other thought processes) drugs have been used clinically and have improved the negative symptoms of some patients, the overall effect is limited. Many patients still cannot recover and repair their normal social functions due to the negative symptoms, which makes it difficult to resume normal social work. Besides, the treatment of cognitive impairment is also a focus of schizophrenia treatment at present, since cognitive impairment affects the verbal memory, semantic processing ability and attention function of most patients with schizophrenia. However, the improvement of cognitive function by anti-schizophrenia drugs currently under research or on the market is also very limited.

Current anti-schizophrenic drugs, in addition to the problems mentioned above, remain in a dilemma for the treatment of refractory schizophrenia. Refractory schizophrenia refers to a group of patients who can not obtain ideal curative effect after being treated according to general methods. This kind of patients have been treated with three different active ingredients of anti-psychotic drugs in adequate dosage and duration, but have poor response to treatment or are unable to tolerate the adverse effects of anti-psychotic drugs, or whose disease recurs or worsens even with adequate maintenance or preventive treatment. Therefore, anti-refractory schizophrenic drugs has been a difficulty of current clinical drug research and also a direction that needs to be tackled urgently.

In conclusion, anti-schizophrenic drugs with good and consistently effective treatment of negative symptoms, improved cognitive function, effective treatment of refractory schizophrenia, low adverse drug reactions (e.g., extrapyramidal reactions, weight gain, nausea, and vomiting), and multitargeted effects remain a hot research direction in the central nervous system.

CONTENT OF THE PRESENT INVENTION

The present disclosure aims to provide a novel anti-schizophrenic medicament acting on a 5-hydroxytryptamine receptor and/or a dopamine receptor, and the medicament has good antagonistic activity on the 5-HT2A receptor and/or the dopamine D2 receptor and can effectively treat and improve schizophrenia.

The purpose of the present disclosure is to provide a heterocyclic substituted fused γ-carboline derivative with therapeutic activity in psychoneurological diseases, a pharmaceutical composition thereof and a use thereof in the medical field.

The present disclosure provides a compound represented by general formula (I), a stereoisomer thereof or a pharmaceutically acceptable salt thereof, (I)

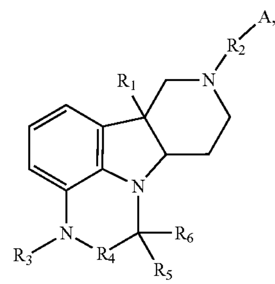

wherein, $R_1$ is independently C1-C6 alkyl optionally substituted by halogen, C1-C3 alkoxy, cyano, amino, nitro, hydroxyl, C2-C4 alkenyl, C2-C4 alkynyl or C3-C5 cycloalkyl;

$R_2$ is independently $—R_7—R_8—R_9—$;

$R_3$ is independently any one of hydrogen or C1-C3 alkyl;

$R_4$ is independently any one of $—C(═O)—$ or $—CH_2—$;

$R_5$ and $R_6$ are each independently any one of hydrogen or C1-C3 alkyl optionally substituted by halogen, C1-C3 alkoxy, cyano, amino, nitro, hydroxyl, C2-C4 alkenyl or C2-C4 alkynyl, or $R_5$, $R_6$ and the carbon atom directly attached thereto together form $—C(═O)—$;

$R_7$ is independently C1-C5 alkylene;

$R_8$ is independently any one of $—C(═O)—$, $—CH_2—$ or $—O—$;

$R_9$ is independently any one of C1-C3 alkylene or absence;

A is phenyl optionally substituted by one or more halogens.

In one embodiment of the present disclosure, the $R_1$ is independently C1-C3 alkyl optionally substituted by halogen, C1-C3 alkoxy, cyano, amino, nitro, hydroxyl, C2-C4 alkenyl, C2-C4 alkynyl or C3-C5 cycloalkyl.

In one embodiment of the present disclosure, the $R_3$ is independently any one of hydrogen or C1-C3 alkyl.

In one embodiment of the present disclosure, the $R_4$ in the compound represented by general formula (I) is $—CH_2—$.

In one embodiment of the present disclosure, the $R_4$ is —C(═O)—.

In one embodiment of the present disclosure, the $R_5$ and $R_6$ are each independently any one of hydrogen or unsubstituted C1-C3 alkyl, or $R_5$, $R_6$ and the carbon atom directly attached thereto together form —C(═O)—.

In one embodiment of the present disclosure, the $R_5$ and $R_6$ are each independently hydrogen.

In one embodiment of the present disclosure, the $R_4$ in the compound represented by general formula (I) is $—CH_2—$; the $R_5$ and $R_6$ are each independently hydrogen.

In one embodiment of the present disclosure, the A is independently phenyl substituted by one or more halogens.

In one embodiment of the present disclosure, the $R_1$ is independently unsubstituted C1-C3 alkyl.

In one embodiment of the present disclosure, the $R_3$ is independently any one of hydrogen or unsubstituted C1-C3 alkyl.

In one embodiment of the present disclosure, C1-C3 alkyl in the optionally substituted C1-C3 alkyl is selected from any one of methyl, ethyl or propyl.

In one embodiment of the present disclosure, the unsubstituted C1-C3 alkyl is selected from any one of methyl, ethyl or propyl.

In one embodiment of the present disclosure, the C1-C5 alkylene is selected from C3-C5 alkylene.

In one embodiment of the present disclosure, the C1-C3 alkylene is selected from C1-C2 alkylene.

In one embodiment of the present disclosure, the halogen is any one of fluorine, chlorine, bromine or iodine.

In one embodiment of the present disclosure, the compound represented by general formula (I) is selected from a compound represented by the following general formula (I-A):

(I-A)

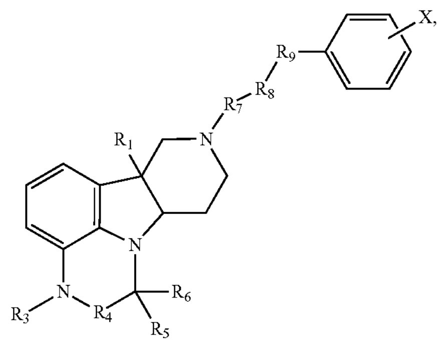

wherein,

X is halogen; any substitutable position of the benzene ring is substituted by X; the number of X is one or more, preferably one;

$R_1$, $R_3$, $R_4$, $R_5$, $R_6$, $R_7$, $R_8$ and $R_9$ are as defined above.

In one embodiment of the present disclosure, the halogen is any one of fluorine, chlorine, bromine or iodine, preferably fluorine.

In one embodiment of the present disclosure, the compound represented by general formula (I) is selected from a compound represented by the following general formula (I-B):

(I-B)

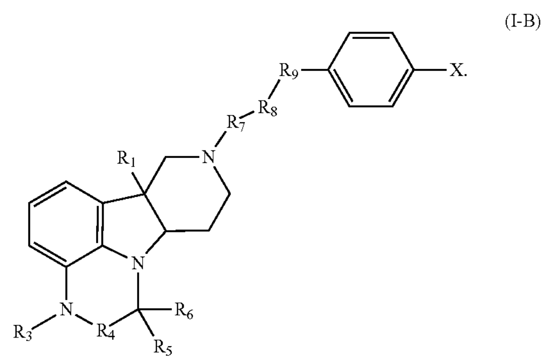

$R_1$, $R_3$, $R_4$, $R_5$, $R_6$, $R_7$, $R_8$, $R_9$ and X are as defined above.

In one embodiment of the present disclosure, the compound represented by general formula (I) is selected from a compound represented by the following general formula (I-B):

(I-B)

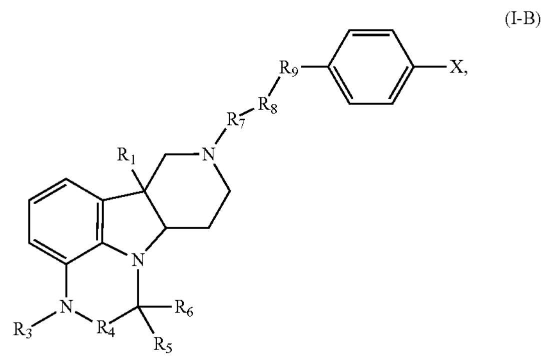

wherein, $R_1$ is independently any one of methyl, ethyl or propyl;

$R_3$ is independently any one of hydrogen, methyl, ethyl or propyl;

$R_4$ is independently any one of —C(═O)— or $—CH_2—$;

$R_5$ and $R_6$ are each independently any one of hydrogen, methyl or ethyl, or $R_5$, $R_6$ and the carbon atom directly attached thereto together form —C(═O)—;

$R_7$ is independently any one of $—CH_2—CH_2—$, $—CH_2—CH_2—CH_2—$ or $—CH_2—CH_2—CH_2—CH_2—$;

$R_8$ is independently any one of —C(═O)—, $—CH_2—$ or —O—;

$R_9$ is independently any one of $—CH_2—CH_2—$, $—CH_2—$ or absence;

X is independently any one of fluorine or chlorine.

In one embodiment of the present disclosure, the $C_2$-$C_4$ alkenyl includes but is not limited to $—CH_2═CH_2$, $—CH_2—CH═CH_2$, $—CH═CH—CH_2$, $—CH═CH—CH_2—CH_2$, $—CH_2—CH═CH—CH_2$, $—CH_2—CH—CH═CH$, etc.

In one embodiment of the present disclosure, the C2-C4 alkenyl is preferably C2-C3 alkenyl, and selected from any one of $—CH_2═CH_2$, $—CH_2—CH═CH_2$ or $—CH═CH—CH_2$.

In one embodiment of the present disclosure, the C2-C4 alkynyl includes but is not limited to —C≡C, $—CH_2—C≡C$, $—C≡C—CH_2$, $—C≡C—CH_2—CH_2$, $—CH_2C≡C—CH_2$, $—CH_2—CH—C≡C$, etc.

In one embodiment of the present disclosure, the C2-C4 alkynyl is preferably C2-C3 alkynyl, and selected from any one of —C≡C, —$CH_2$—C≡C, or —C≡C—$CH_2$.

In one embodiment of the present disclosure, the C1-C3 alkoxy is selected from any one of —O—$CH_3$, —O—$CH_2$—$CH_3$, —O—$CH_2$—$CH_2$—$CH_3$, —O—CH($CH_3$)—$CH_3$, preferably any one of —O—$CH_3$ or —O—$CH_2$—$CH_3$.

In one embodiment of the present disclosure, the alkylene is a saturated aliphatic hydrocarbon straight chain group with 1-20 carbon atoms, and the C1-C5 alkylene in the present disclosure is any one of —$CH_2$—, —$CH_2$—$CH_2$—, —$CH_2$—$CH_2$—$CH_2$, —$CH_2$—$CH_2$—$CH_2$—$CH_2$, —$CH_2$—$CH_2$—$CH_2$—$CH_2$—$CH_2$— or —$CH_2$—$CH_2$—$CH_2$—$CH_2$—$CH_2$—; the C1-C3 alkylene is any one of —$CH_2$—, —$CH_2$—$CH_2$— or —$CH_2$—$CH_2$—$CH_2$—; the C1-C2 alkylene is any one of —$CH_2$— or —$CH_2$—$CH_2$—.

In one embodiment of the present disclosure, the compound represented by general formula (I) is selected from a compound represented by the following general formula (I-C):

(I-C)

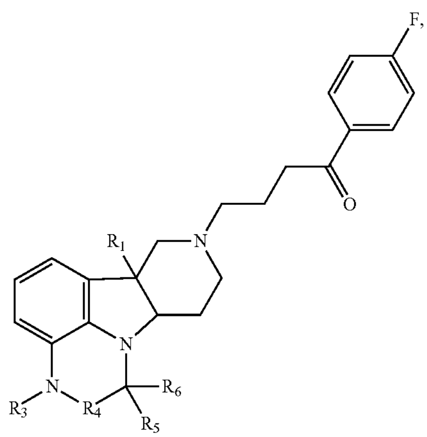

wherein, $R_1$ is independently any one of methyl, ethyl or propyl;

$R_3$ is independently any one of methyl, ethyl or propyl;

$R_4$ is independently any one of —C(═O)— or —$CH_2$—;

$R_5$ and $R_6$ are each independently any one of hydrogen, methyl or ethyl, or $R_5$, $R_6$ and the carbon atom directly attached thereto together form —C(═O)—.

In one embodiment of the present disclosure, the compound represented by general formula (I), the stereoisomer thereof or the pharmaceutically acceptable salt thereof, is selected from any one of the following specific compounds:

1

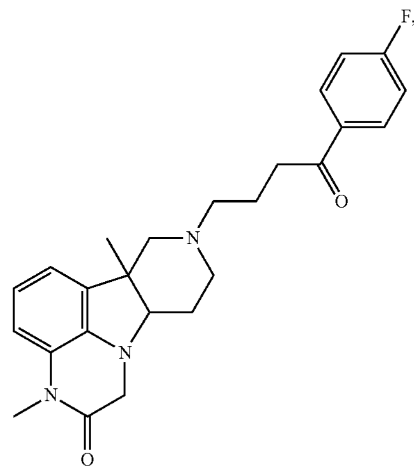

1-A

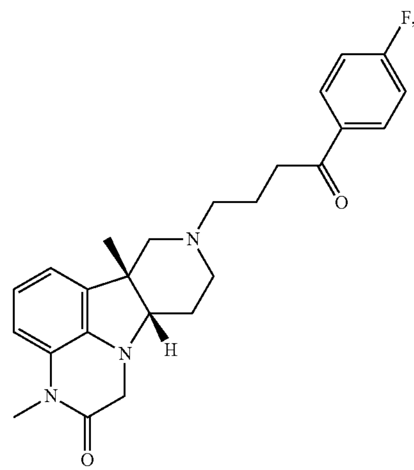

1-B

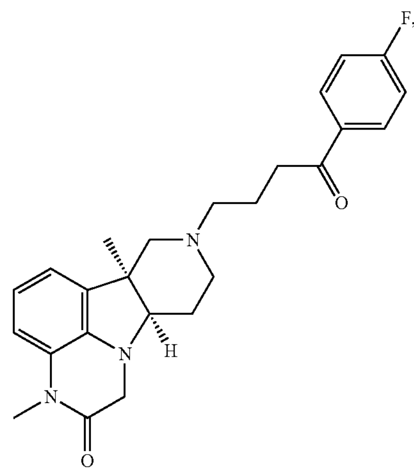

-continued
2
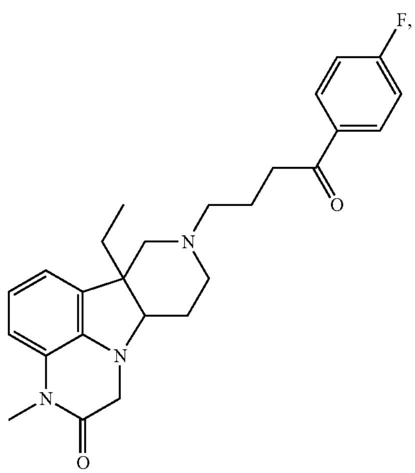
3
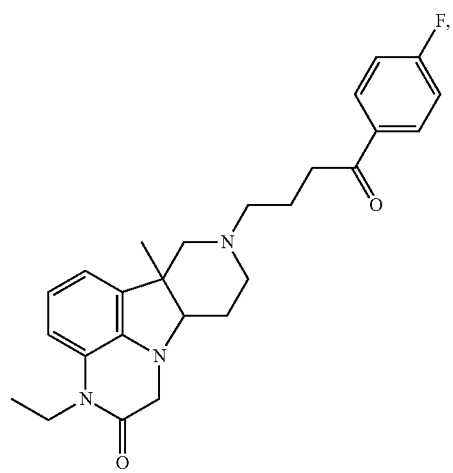
2-A
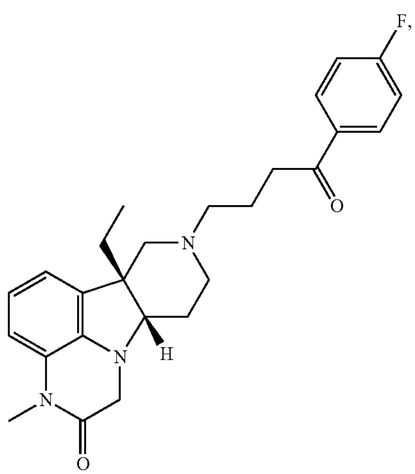
3-A
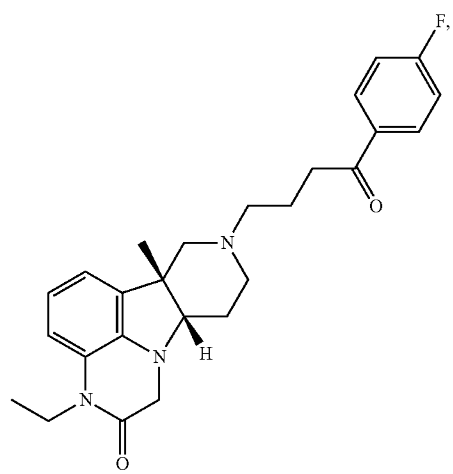
2-B
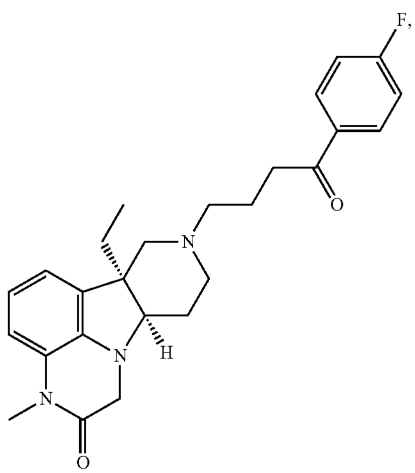
3-B
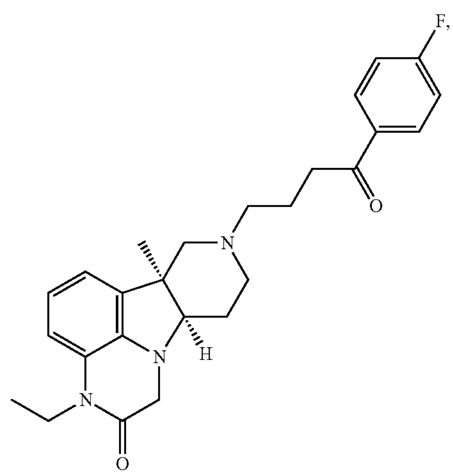
-continued -continued
4
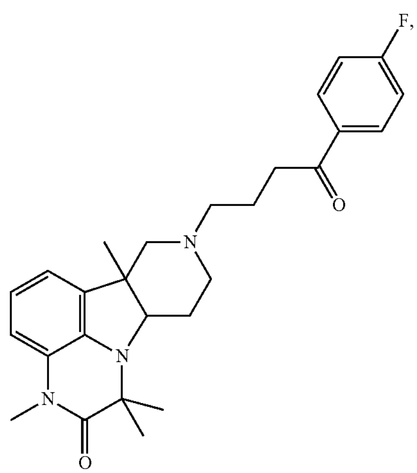
4-A
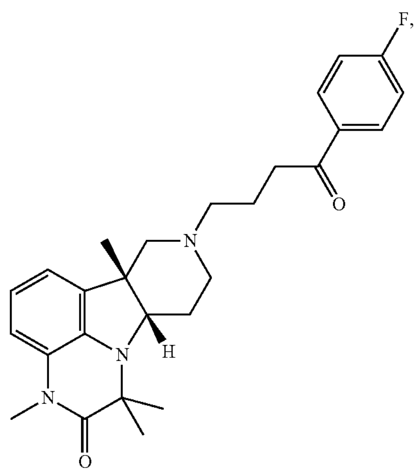
4-B
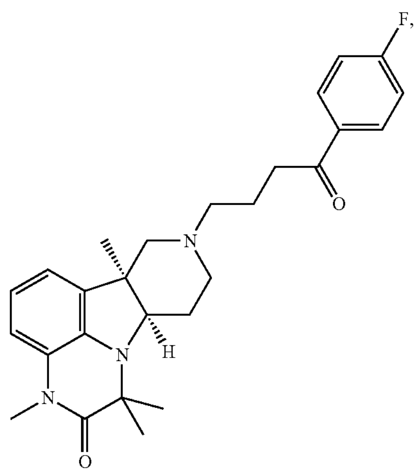
-continued
5
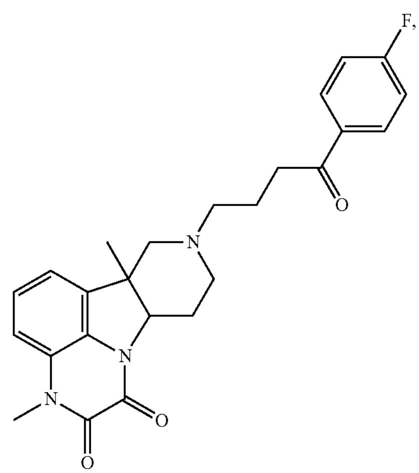
5-A
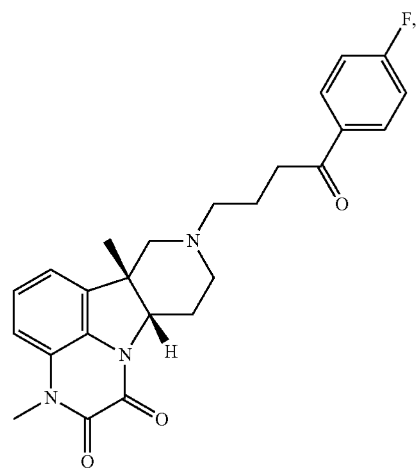
5-B
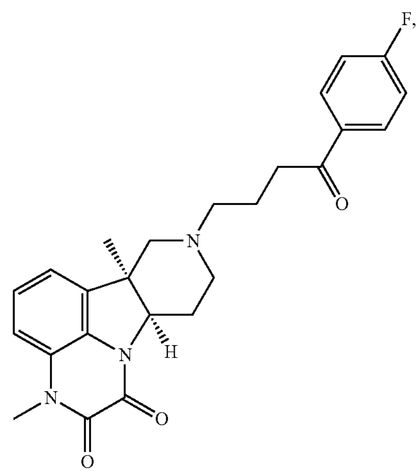

-continued

6

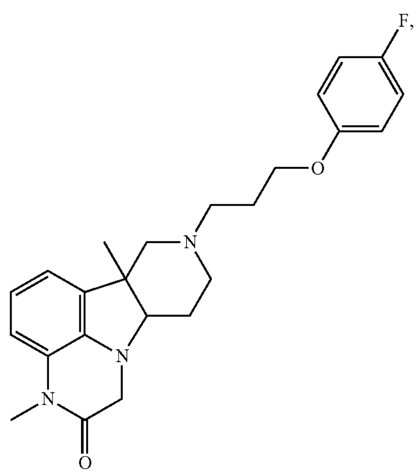

6-A

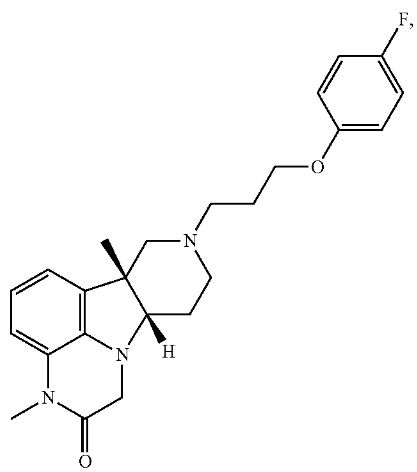

6-B

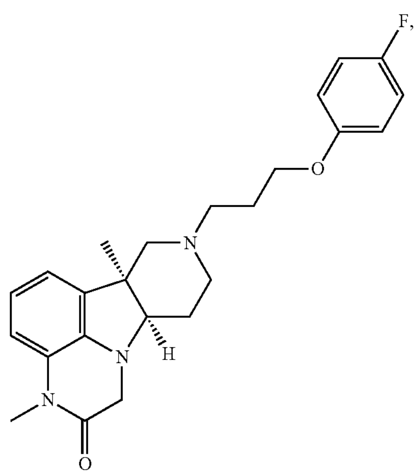

-continued

7

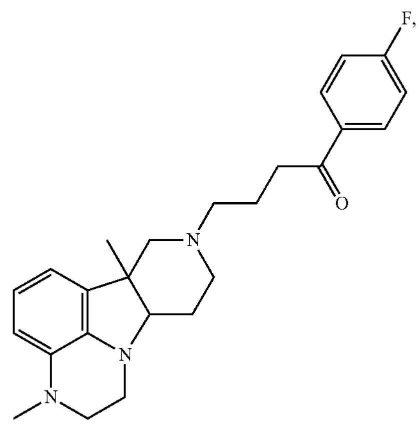

7-A

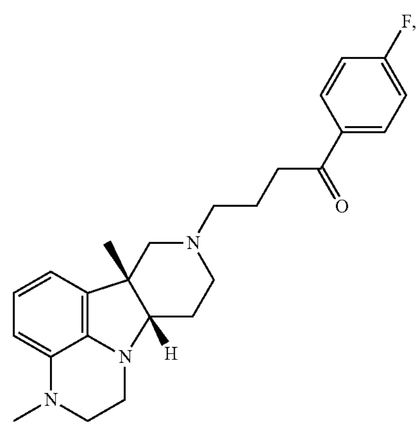

7-B

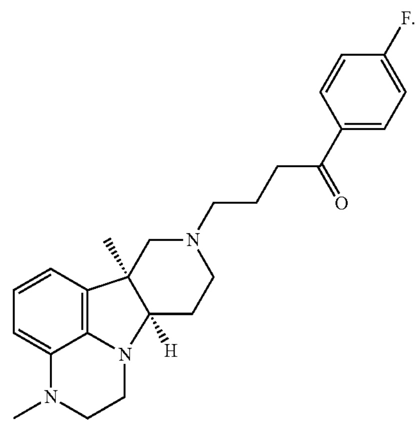

In one embodiment of the present disclosure, the pharmaceutically acceptable salt of any one of the compound represented by general formula (I) is selected from fumarate, maleate, phosphate, nitrate, sulfate, benzenesulfonate or oxalate.

The present disclosure also provides a compound represented by general formula (I-D), a stereoisomer thereof or a pharmaceutically acceptable salt thereof, (I-D)

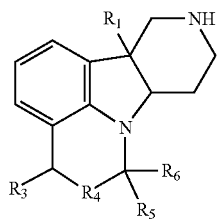

wherein, $R_1$, $R_3$, $R_4$, $R_5$ and $R_6$ are as defined above.

In one preferred embodiment of the present disclosure, in the compound represented by general formula (I-D), $R_1$ is independently any one of methyl, ethyl or propyl;

$R_3$ is independently any one of methyl, ethyl or propyl;

$R_4$ is independently any one of —C(═O)— or —$CH_2$—;

$R_5$ and $R_6$ are each independently any one of hydrogen, methyl or ethyl, or $R_5$, $R_6$ and the carbon atom directly attached thereto together form —C(═O)—.

The present disclosure provides a method for preparing the compound represented by general formula (I), the general formula (I-A), the general formula (I-B) or the general formula (I-C), the stereoisomer thereof or the pharmaceutically acceptable salt thereof, wherein the method uses the compound represented by the general formula (I-D) as a starting material or an intermediate; the method may include the following steps:

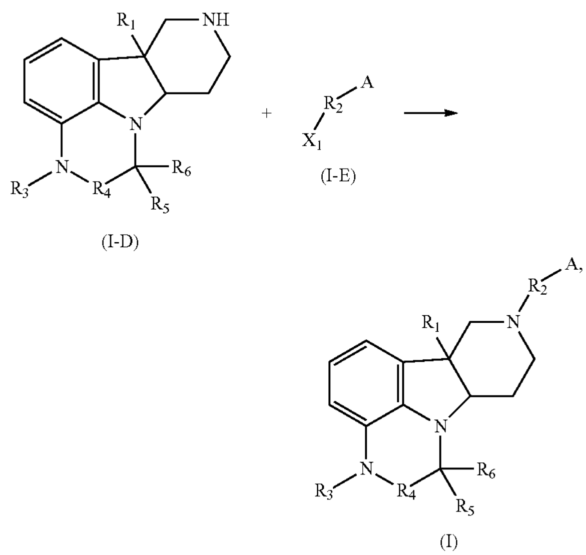

(I-D) (I-E) (I)

preparing the compound represented by general formula (I) by a nucleophilic substitution reaction between a compound of general formula (I-D) and a compound of general formula (I-E);

wherein, $X_1$ is halogen and is selected from fluorine, chlorine, bromine or iodine, preferably chlorine;

$R_1$, $R_2$, $R_3$, $R_4$, $R_5$, $R_6$ and A are as defined above.

In one embodiment of the present disclosure, the method for preparing the compound represented by general formula (I-C), the stereoisomer thereof, or the pharmaceutically acceptable salt thereof comprises the following steps:

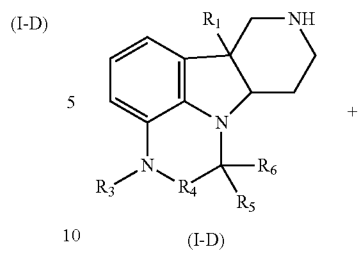

(I-D)

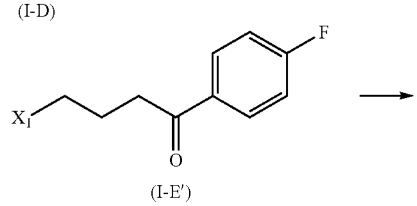

(I-E')

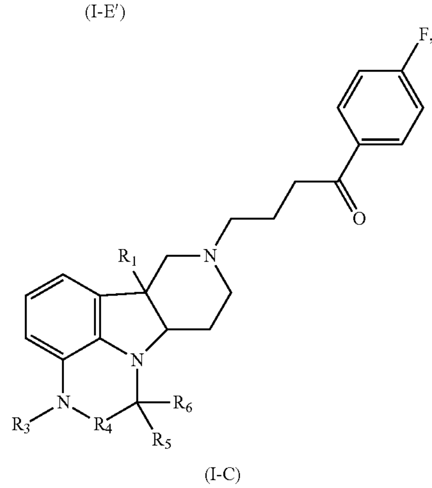

(I-C)

the compound represented by the general formula (I-C) is prepared by a nucleophilic substitution reaction between the compound of general formula (I-D) and a compound of general formula (I-E');

wherein, $X_1$ is halogen and is selected from fluorine, chlorine, bromine or iodine, preferably chlorine;

$R_1$, $R_3$, $R_4$, $R_5$ and $R_6$ are as defined above.

The present disclosure also provides a pharmaceutical composition comprising a therapeutically effective amount of the compound represented by general formula (I), the stereoisomer thereof or the pharmaceutically acceptable salt thereof, and a pharmaceutically acceptable carrier.

In one embodiment of the present disclosure, the pharmaceutical composition may be formulated in a conventional manner using one or more pharmaceutically acceptable carriers. Thus, the active compound of the present disclosure can be formulated into dosage forms for oral, oral-inclusion administration, intranasal, parenteral (e.g., intravenous, intramuscular or subcutaneous), or rectal administration, or for dosage forms suitable for administration by inhalation or insufflation. The compound of the present disclosure or the pharmaceutically acceptable salt thereof may also be formulated into sustained-release dosage forms.

In one embodiment of the present disclosure, an effective dose of the compound of the present disclosure or the pharmaceutically acceptable salt thereof may be administered orally together with, for example, an inert diluent or some kind of carrier. According to some embodiments of the present disclosure, the compound of the present disclosure may be wrapped in gelatin capsules or pressed into tablets. For the purpose of oral therapy, the compound of the present disclosure may be used together with an excipient and in the form of tablets, lozenges, capsules, suspensions, syrups, etc. According to embodiment of the present disclosure, the above formulation should contain at least 0.5% (w/w) of the active compound of the present disclosure, but it can be varied according to the specific dosage form, with 4% to about 70% of the unit weight being convenient. The amount of active compound in such a pharmaceutical composition should reach an appropriate dose.

In one embodiment of the present disclosure, with respect to oral administration, the active compound of the present disclosure may be formulated into tablets or capsules, for example, by conventional means with a pharmaceutically acceptable excipient, such as a binder, a filler, a lubricant, a disintegrant or a wetting agent. Tablets may be coated by methods well known in the art. Liquid formulations for oral administration may use solutions, syrups or suspensions, or volatile into a dry product, which can be regenerated with water or other suitable carriers before use. Such liquid formulations may be prepared by conventional means using a pharmaceutical additive such as a suspending agent, an emulsifier, a non-aqueous carrier and a preservative.

In one embodiment of the present disclosure, when the active compound of the present disclosure is used for parenteral administration, then the compound provided by the present disclosure may be combined with sterile water or organic media to form an injectable solution or suspension.

In one embodiment of the present disclosure, the active compound of the present disclosure may be formulated into a rectal composition, such as a suppository or a retention enema, for example, containing a conventional suppository base, such as cocoa butter or other glyceride.

The present disclosure also provides a use of the compound represented by general formula (I), the stereoisomer thereof, the pharmaceutically acceptable salt thereof or the pharmaceutical composition thereof in the manufacture of a medicament involving or regulating a 5-hydroxytryptamine receptor, a serotonin transporter (SERT) and/or a dopamine receptor, preferably a use in the manufacture of a medicament involving or regulating a 5-HT2A receptor, a serotonin transporter, a dopamine D1 receptor and/or a dopamine D2 receptor, and more preferably a use in the manufacture of a medicament involving or regulating the 5-HT2A receptor and/or the dopamine D2 receptor. Herein, the medicament optionally comprises one or more additional active agents that regulate the mammalian nervous system or alleviate psychiatric disease.

In one embodiment of the present disclosure, the regulation (regulating) includes, but is not limited to, inhibitory activity or antagonistic activity to the receptor.

In one embodiment of the present disclosure, the present disclosure also provides a use of the compound represented by general formula (I), the stereoisomer thereof or the pharmaceutically acceptable salt thereof in the manufacture of a medicament for treating a neuropsychiatric disease.

In one embodiment of the present disclosure, the neuropsychiatric disease is selected from one or more of depression (such as major depressive disorder (MDD)), anxiety disorder, dementia, schizophrenia, sleep disorder, dyskinesia, behavioral disorder of dementia patient, Parkinson's disease, Alzheimer's disease, migraine, hyperactivity disorder (such as attention deficit hyperactivity disorder), obsessive-compulsive disorder, social phobia, neurodegenerative disease, bipolar disorder, post-traumatic stress syndrome, addictive disorder, withdrawal syndrome or attention deficit.

In one embodiment of the present disclosure, the neuropsychiatric diseases described in the present disclosure is preferably any one or more of depression (such as major depressive disorder MDD), anxiety disorder, dementia, schizophrenia, sleep disorder, dyskinesia, behavioral disorder of dementia patients, neurodegenerative disease or bipolar disorder, and more preferably one or more of depression, anxiety disorder, schizophrenia or neurodegenerative disease.

In one embodiment of the present disclosure, the neuropsychiatric disease is preferably schizophrenia.

The present disclosure further relates to a method for treating, alleviating and/or preventing a disease involving a 5-hydroxytryptamine receptor, a serotonin transporter (SERT) and/or a dopamine receptor, and the method comprises administering a therapeutically effective dose of the compound represented by general formula of the present disclosure or the pharmaceutically acceptable salt thereof to a subject in need thereof; preferably, the present disclosure relates to a method for treating, alleviating or preventing a disease involving a 5-HT2A receptor, the serotonin transporter, a dopamine D1 receptor and/or a dopamine D2 receptor, and the method comprises administering a therapeutically effective dose of the compound represented by general formula of the present disclosure or a pharmaceutically acceptable salt thereof to a subject in need thereof. In some embodiments of the present disclosure, the 5-hydroxytryptamine receptor is preferably the 5-HT2A receptor and the dopamine receptor is preferably the dopamine D2 receptor. The method shows outstanding curative effects and less side effects.

In some embodiments of the present disclosure, the present disclosure relates to a method for treating, alleviating and/or preventing a neuropsychiatric disease, and the method comprises administering a therapeutically effective dose of the compound represented by the general formula of the present disclosure or the pharmaceutically acceptable salt thereof to a subject in need thereof.

In some preferred embodiments of the present disclosure, the neuropsychiatric disease is selected from any one or more of depression (such as major depressive disorder), anxiety disorder, dementia, schizophrenia, sleep disorder, dyskinesia, behavioral disorder of dementia patient, Parkinson's disease, Alzheimer's disease, migraine, hyperactivity disorder (such as attention deficit hyperactivity disorder), obsessive-compulsive disorder, social phobia, neurodegenerative disease, bipolar disorder, post-traumatic stress syndrome, addictive disorder, withdrawal syndrome or attention deficit, preferably any one or more of depression (such as major depressive disorder), anxiety disorder, dementia, schizophrenia, sleep disorder, dyskinesia, behavioral disorder of dementia patient, neurodegenerative disease or bipolar disorder.

Unless otherwise defined, all technical and scientific terms used herein have the same meaning as commonly understood by those of ordinary skill in the art to which the present disclosure belongs. In case of contradiction, the definition provided in the present disclosure shall prevail. When a trading name appears herein, then it is intended to refer to its corresponding commodity or an active ingredient thereof. All patents, published patent applications and publications cited herein are incorporated herein by reference.

The term "optional", "optionally" or "optionally exist" means that the event or condition subsequently described may occur but not requisite, and that the description includes an instance in which the event or condition occurs and an instance in which the event or condition does not occur. For example, "optionally existing bond" means that the bond may or may not exist, and the description includes a single bond, a double bond, a triple bond, etc.

The terms "comprising", "including", "having", "containing" or "involving" are open-ended expressions that include what is specified in the present disclosure, but do not exclude other aspects. It should be understood that the terms such as "comprising" can cover a closed meaning, that is, "consisting of . . . ".

As described in the present disclosure, the compound of the present disclosure may optionally be substituted by one or more substituents, as the compound of general formula or specific examples and subclasses in the embodiments. It should be understood that the term "optionally substituted" and the term "substituted or unsubstituted" can be used interchangeably. In general, the term "substituted" indicates that one or more hydrogen atoms in a given structure are substituted with a specific substituent. Unless otherwise indicated, the optionally substituted group may be substituted at each of the substitutable positions of the group. When more than one position in the given structural formula can be substituted by one or more substituents selected from the specific group, then the substituents can be substituted equally or differently at each position.

In addition, it should be noted that, unless otherwise explicitly stated, the description "respectively and independently" used in the present disclosure should be understood in a broad sense, which can mean that the specific options expressed between the same symbols in different groups do not affect each other, or that the specific options expressed between the same symbols in the same groups do not affect each other.

Both "Z" and "—Z—" herein are denoted as the same specific group and can be used interchangeably.

The expressions "X is selected from A, B or C", "X is selected from A, B and C", "X is A, B or C", "X is A, B and C" and other different terms used herein all express the same meaning, which means that X can be any one or more of A, B, C.

When any variable (such as R) and variable with markers (such as $R_1$, $R_2$, $R_3$, $R_4$, $R_5$, $R_6$ and $R_7$) occur in the constitution or structure of the compound more than once, then the definition of the variable at each occurrence is independent. For example, if a group is substituted with 0, 1, 2, 3 or 4 R substituents, the group can be optionally substituted with up to four R substituents, and the options for each R substituents at each occurrence are independent of each other.

The term "pharmaceutically acceptable" substance refers to a substance that, within the normal medical judgment, is suitable for contact with the patient's tissues without inappropriate toxicity, irritation, allergic reaction, etc., and the substance has a reasonable ratio of advantages and disadvantages, and can be effectively used for its purpose.

The term "pharmaceutically acceptable salt" refers to the salt of the compound of the present disclosure, and the salt is safe and effective when used in mammals and has due biological activity.

The term "pharmaceutically acceptable carrier" refers to those substances that have no obvious stimulating effect on organisms and may not damage the biological activity and performance of the active compound. "Pharmaceutically acceptable carrier" includes but is not limited to, glidant, sweetener, diluent, preservative, dye/colorant, flavoring agent, surfactant, wetting agent, dispersant, disintegrant, stabilizer, solvent or emulsifier.

The terms "administration", "giving" and the like refer to methods that enable the compound or the composition to be delivered to a desired biological action site. The methods include, but are not limited to, oral or parenteral (including intracerebroventricular, intravenous, subcutaneous, intraperitoneal, intramuscular, intravascular injection or infusion), topical, rectal administration, etc., especially injection or oral administration.

As used herein, the term "treatment" includes alleviating, mitigating or improving diseases or symptoms, preventing other symptoms, improving or preventing the underlying metabolic factors of symptoms, inhibiting diseases or symptoms, for example, stopping the development of diseases or symptoms, mitigating diseases or symptoms, promoting the alleviation of diseases or symptoms, or stopping the symptoms of diseases or symptoms, and extending to include prevention. "Treatment" also includes the realization of therapeutic benefit and/or preventive benefit. Therapeutic benefit refers to the eradication or improvement of the treated diseases. In addition, therapeutic benefit is achieved by eradicating or improving one or more physiological symptoms related to underlying diseases. Although patients may still have underlying diseases, the improvement of patients' diseases can be observed. Preventive benefit refers to the use of the composition by patients to prevent the risk of a certain disease, or when patients develop one or more physiological symptoms of the disease, although the disease has not been diagnosed.

The term "active ingredient", "therapeutic agent", "active substance" or "active agent" refers to a chemical entity that can effectively treat or prevent a target disorder, disease or disorder.

The term "neuropsychiatric disease" refers to the general term of neurological disease and psychiatric disease, including neurological disease and/or psychiatric disease.

For medicament, medicament unit or active ingredient, the terms "effective amount", "therapeutically effective amount" or "preventively effective amount" refer to a sufficient amount of a medicament or formulation with acceptable side effects but capable of achieving the desired effect. The determination of effective amount varies from person to person, and depends on the age and general condition of the individual, and also depends on the specific active substance, and the appropriate effective amount in a case may be determined by the person skilled in the art according to routine tests.

As used herein, "individual" includes a human or a non-human animal. Exemplary human individual include human individual (called patient) suffering from disease (such as the disease described herein) or normal individual. "Non-human animal" in the present disclosure includes all vertebrate, such as non-mammal (such as bird, amphibian and reptile) and mammal, such as non-human primate, domestic animal and/or domesticated animal (such as sheep, dog, cat, cow and pig).

In each part of the specification, the substituents of the compound disclosed in the present application are disclosed according to the type or range of the group. In particular, the present disclosure includes each independent secondary combination of individual members of these group types and ranges. For example, the term "C1-C6 alkyl" particularly refers to the independently disclosed methyl, ethyl, C3 alkyl, C4 alkyl, C5 alkyl and C6 alkyl. Examples of alkyl include, but are not limited to, methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), isobutyl (i-Bu, $—CH_2CH(CH_3)_2$), sec-butyl (s-Bu, —CH $(CH_3)CH_2CH_3)$, tert-butyl (t-Bu, $—C(CH_3)_3)$, n-pentyl $(—CH_2CH_2CH_2CH_2CH_3)$, 2-pentyl $(—CH(CH_3)CH_2CH_2CH_3)$, 3-pentyl $(—CH(CH_2CH_3)_2)$, 2-methyl-2-butyl $(—C(CH_3)_2CH_2CH_3)$, 3-methyl-2-butyl $(—CH(CH_3)CH(CH_3)_2)$, 3-methyl-1-butyl $(—CH_2CH_2CH(CH_3)_2)$, 2-methyl-1-butyl $(—CH_2CH(CH_3)CH_2CH_3)$, n-hexyl $(—CH_2CH_2CH_2CH_2CH_2CH_3)$, 2-hexyl $(—CH(CH_3)CH_2CH_2CH_2CH_3)$, 3-hexyl $(—CH(CH_2CH_3)(CH_2CH_2CH_3))$, 2-methyl-2-pentyl $(—C(CH_3)_2CH_2CH_2CH_3)$, 3-methyl-2-pentyl $(—CH(CH_3)CH(CH_3)CH_2CH_3)$, 4-methyl-2-pentyl $(—CH(CH_3)CH_2CH(CH_3)_2)$, 3-methyl-3-pentyl $(—C(CH_3)(CH_2CH_3)_2)$, 2-methyl-3-pentyl $(—CH(CH_2CH_3)CH(CH_3)_2)$, 2,3-dimethyl-2-butyl $(—C(CH_3)_2CH(CH_3)_2)$, 3,3-dimethyl-2-butyl $(—CH(CH_3)C(CH_3)_3)$, n-heptyl, n-octyl, etc.

The term "hydrogen (H)" refers to a single hydrogen atom. Such an atomic group may be attached to other groups, for example, it can be attached to oxygen atom to form a hydroxyl group.

The term "halogen" refers to fluorine (F), chlorine (Cl), bromine (Br) or iodine (I).

The term "aryl" refers to monocyclic, bicyclic and tricyclic carbocyclic systems containing 6-14 ring atoms, or 6-12 ring atoms, or 6-10 ring atoms, and at least one ring is aromatic. The aryl group is usually, but not necessarily, attached to the parent molecule through the aromatic ring of the aryl group. Examples of the aryl group may include phenyl, naphthyl and anthracene. The aryl group is optionally substituted by one or more substituents described in the present disclosure.

Examples of alkoxy group include, but are not limited to, methoxy (MeO, $—OCH_3$), ethoxy (EtO, $—OCH_2CH_3$), 1-propoxy (n-PrO, n-propoxy, $—OCH_2CH_2CH_3$), 2-propoxy (i-PrO, i-propoxy, $—OCH(CH_3)_2$), 1-butoxy (n-BuO, n-butoxy, $—OCH_2CH_2CH_2CH_3$), 2-methyl-1-propoxy (i-BuO, i-butoxy, $—OCH_2CH(CH_3)_2$), 2-butoxy (s-BuO, s-butoxy, $—OCH(CH_3)CH_2CH_3$), 2-methyl-2-propoxy (t-BuO, t-butoxy, $—OC(CH_3)_3$), 1-pentoxy (n-pentyloxy, $—OCH_2CH_2CH_2CH_2CH_3$), 2-pentyloxy $(—OCH(CH_3)CH_2CH_2CH_3)$, 3-pentyloxy $(—OCH(CH_2CH_3)_2)$.

The term "—C(=O)—" refers to the carbonyl.

The following detailed description of the disclosure is intended to illustrate non-limiting embodiments to enable others skilled in the art to more fully understand the technical solutions of the present disclosure, a principle thereof and a practical use thereof, so that others skilled in the art may modify and implement the present disclosure in many forms, and so that the present disclosure can best adapt to the requirements of specific use.

BENEFICIAL TECHNICAL EFFECTS OF THE PRESENT DISCLOSURE

The compound provided by the present disclosure is an antagonist acting on $5\text{-HT}_{2A}$ receptor and/or $D_2$ receptor, and the compound has good antagonistic effect on $5\text{-HT}_{2A}$ receptor and/or $D_2(D_{2L}, D_{2S})$ receptor; and/or the compound has a relatively high $D_2/5\text{-HT}_{2A}$ ratio and has good selectivity; and/or the compound has good pharmacokinetic properties; and/or the compound has good in-vivo efficacy; and/or the compound is not only as effective as traditional antipsychotic for positive symptom, but also has stronger improvement effect on negative symptom and cognitive deficit symptom with lower side effects (such as reducing the possibility of inducing EPS reaction).

DETAILED DESCRIPTION OF THE PREFERRED EMBODIMENT

Embodiments of the present disclosure have been described in detail below. The embodiments described below are exemplary and are only used to explain the present disclosure, but they cannot be understood as a limitation of the present disclosure. Unless otherwise specified, the proportion and percentage referred to herein are calculated by weight.

SYNTHETIC EMBODIMENTS

Embodiment 1: 8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxalin-2(3H)-one (Compound 1)

Step 1: Preparation of 4-nitroso-3,4-dihydroquinoxalin-2(1H)-one (Intermediate 1-2)

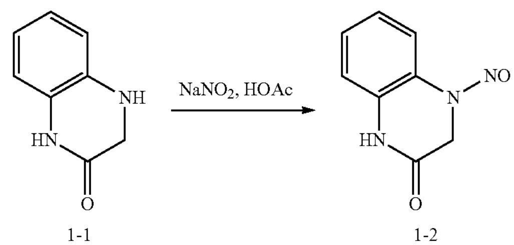

1-1

1-2

The raw material of 3,4-dihydroquinoxalin-2(1H)-one (2.3 g, 16 mmol) was dissolved in a mixed solvent of acetic acid and water (25/12 mL), and in an ice bath, an aqueous solution (12 mL) of sodium nitrite (1.1 g, 16 mmol) was slowly added thereto in dropwise. The reaction was carried out for 2 hours by keeping the temperature, then the reaction mixture was filtered under reduced pressure, and the filter cake was washed with water (12 mL) and dried to obtain intermediate 1-2, yellow solid 2.2 g, yield: 81%. LCMS m/z $(M+H)^+$: 178.1.

Step 2: Preparation of 4-amino-3,4-dihydroquinoxalin-2(1H)-one hydrochloride (Intermediate 1-3)

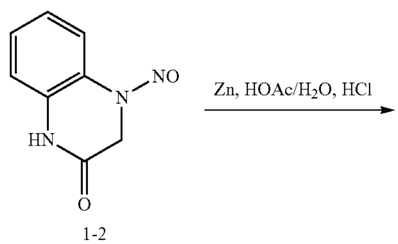

1-2

-continued

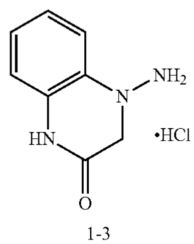

1-3

The intermediate 1-2 (1.5 g, 8.47 mmol) was dissolved in a mixed solvent of glacial acetic acid and water (25/25 mL), and zinc powder (3.0 g, 46.1 mmol) was slowly added thereto in an ice bath. After the reaction was carried out for 30 minutes by keeping the temperature, the reaction mixture was transferred to room temperature and continuously stirred for 2 hours. Then the reaction mixture was filtered and concentrated, and the concentrate was redissolved in ethyl acetate (100 mL) and then stirred for 30 minutes. The reaction mixture was filtered again, and the filtrate was dried, added with 4N dioxane solution of hydrogen chloride (3 mL) and stirred for 30 minutes, then the reaction mixture was concentrated to obtain intermediate 1-3, 1.5 g of crude yellow solid, which was directly used as raw material in the next step without further purification.

Step 3: Preparation of 6b-methyl-8-(2,2,2-trifluoroacetyl)-6b,7,8,9,10,10a-hexahydro-1H-pyrido[3',4':4,5]pyrrolo[1,2,3-de]quinoxalin-2(3H)-one (Intermediate 1-5)

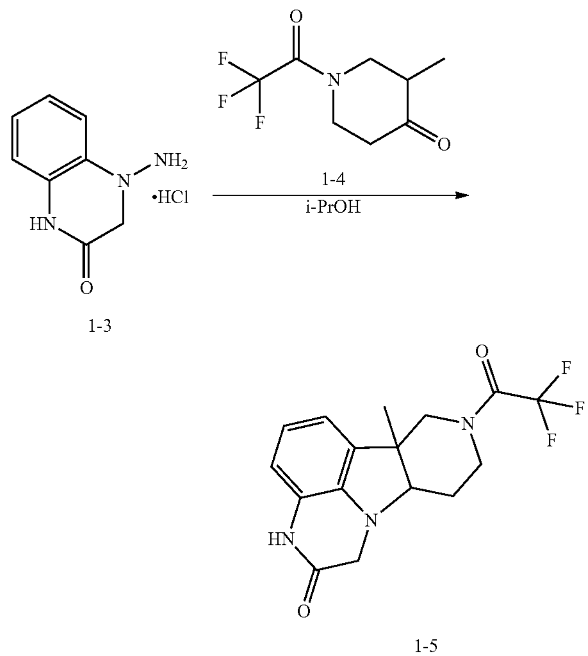

1-3

1-5

Intermediate 1-3 (1.5 g, 7.54 mmol) and intermediate 1-4 (1.4 g, 6.78 mmol) were added to isopropanol (50 mL) and the reaction was carried out at 110° C. for 15 hours. The reaction mixture was cooled to room temperature and concentrated, and the product was separated and purified by column chromatography (DCM/MeOH=1/20) to obtain intermediate 1-5, yellow solid 620 mg, yield: 27%. LCMS m/z $(M+H)^+$: 340.1.

Step 4: Preparation of 3,6b-dimethyl-8-(2,2,2-trifluoroacetyl)-6b,7,8,9,10,10a-hexahydro-1H-pyrido[3',4':4,5]pyrrolo[1,2,3-de]quinoxalin-2(3H)-one (Intermediate 1-6)

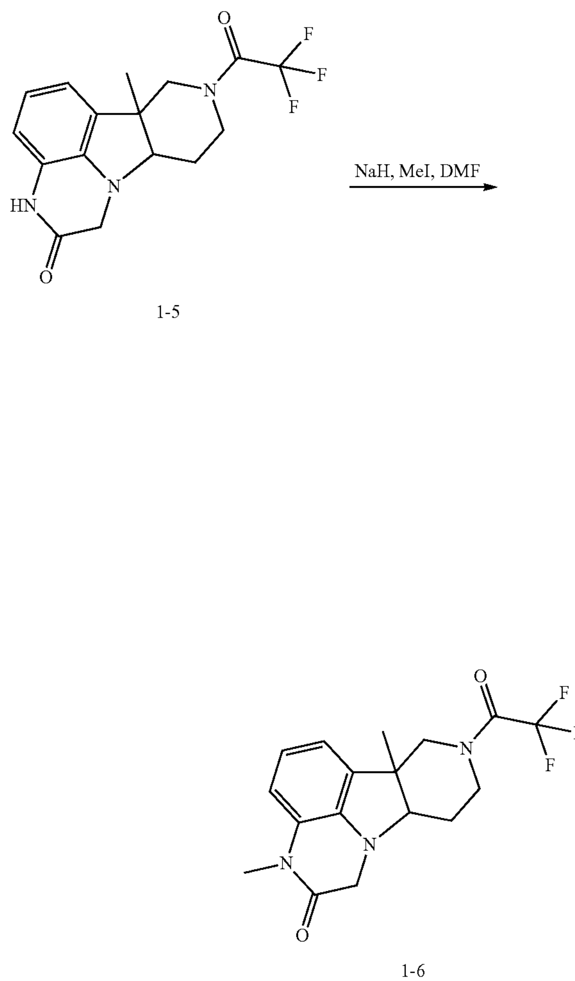

1-5

1-6

Intermediate 1-5 (0.62 g, 1.83 mmol) was dissolved in DMF (10 mL), and sodium hydride (110 mg, 2.75 mmol) was added thereto in an ice bath, and the reaction was carried out for 30 minutes by keeping the temperature. Iodomethane (390 mg, 2.75 mmol) was added to the reaction mixture, then the reaction mixture was transferred to room temperature and stirred for 2 hours. After the reaction was completed, the reaction mixture was placed back in an ice bath, and reaction mixture was quenched by adding water (5 mL), extracted with ethyl acetate (20 mL×3), and then the organic phase was dried over sodium sulfate. The product was separated and purified by column chromatography to obtain a target intermediate 1-6, yellow solid 500 mg, yield: 77%. LCMS m/z $(M+H)^+$: 354.1.

Step 5: Preparation of 3,6b-dimethyl-6b,7,8,9,10,10a-hexahydro-1H-pyrido[3',4':4,5]pyrrolo[1,2,3-de]quinoxalin-2(3H)-one (Intermediate 1-7)

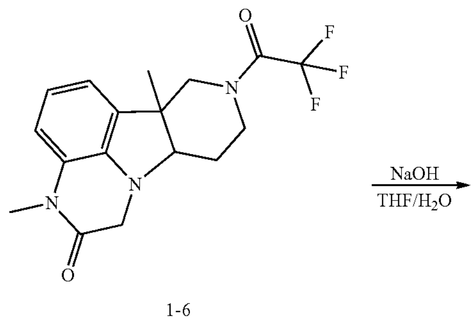

1-6

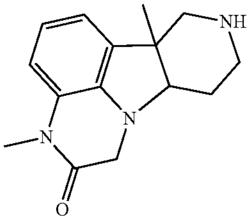

1-7

Intermediate 1-6 (0.5 g, 1.41 mmol) was dissolved in a mixed solvent of tetrahydrofuran and water (50/5 mL), and sodium hydroxide (113 mg, 2.82 mmol) was added to the above mixture. The reaction mixture was reacted at 40° C. for 15 hours, then the reaction mixture was concentrated to remove tetrahydrofuran. The residue was extracted with a mixture of dichloromethane and methanol (10/1, 20 mL×3), and the organic phase was dried over sodium sulfate and purified by column chromatography (DCM/MeOH=10/1-5/1) to obtain a target intermediate 1-7, yellow solid 200 mg, yield: 55%. LCMS m/z $(M+H)^+$: 258.2.

Step 6: Preparation of 8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxalin-2(3H)-one (Compound 1)

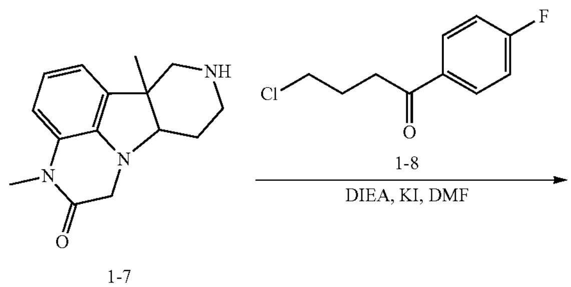

1-7

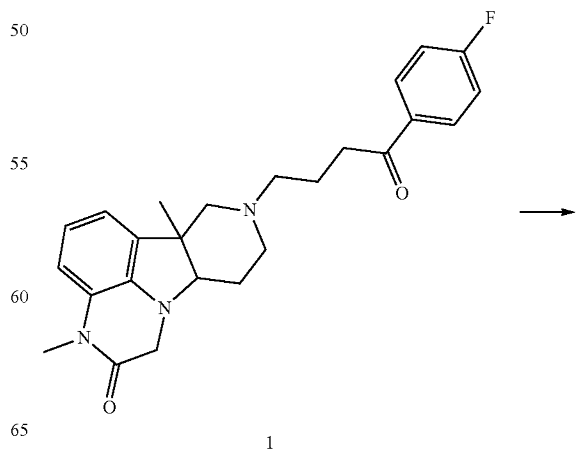

1

-continued

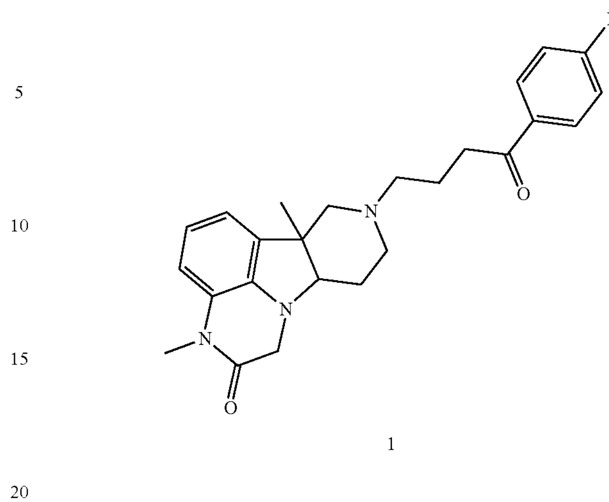

1

Intermediate 1-7 (1.1 g, 4.28 mmol), intermediate 1-8 (1.7 g, 8.56 mmol), potassium iodide (1.4 g, 8.56 mmol) and DIEA (1.1 g, 8.56 mmol) were added to DMF (20 mL), and the reaction mixture was reacted at 78° C. for 3 hours, then the mixture was cooled to room temperature and concentrated directly. The product was prepared by preparative liquid phase ($CH_3CN:H_2O$ (0.1% $NH_4HCO_3$)=10-70%, UV: 214 nm, flow rate: 15 mL/min) to obtain compound 1, off-white solid 245 mg, yield: 13%. LCMS m/z $(M+H)^+$: 422.2.

$^1H$ NMR ($CDCl_3$, 400 MHz): δ 8.06-8.03 (m, 2H), 7.19-7.15 (m, 2H), 6.88-6.76 (m, 3H), 4.45 (d, J=14.4 Hz, 1H), 3.41-3.37 (m, 4H), 3.05-3.02 (m, 2H), 2.95 (s, 1H), 2.71-2.28 (m, 5H), 1.99-1.87 (m, 4H), 1.67-1.50 (m, 4H).

Embodiment 1-A: Preparation of (6bR,10aS)-8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxalin-2(3H)-one (Compound 1-A)

-continued

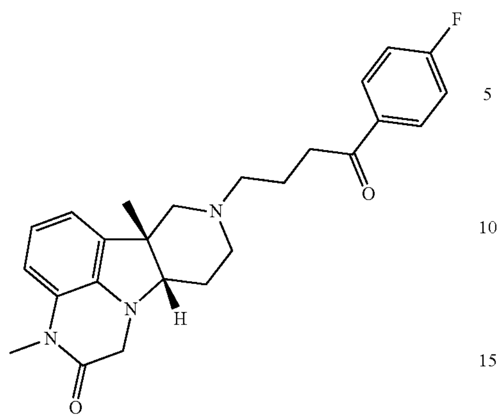

1-A

Compound 1 (1.6 g) was chiral resolved to obtain compound 1-A (427.7 mg). Chiral resolution conditions are as follows:

| | |
|---|---|
| Instrument | Gilson GX-281 |
| Column type | Chiralpak IE 250 mm * 30 mm 5 μm |
| Sample volume | 1500 μL |
| Mobile phase | Hex:EtOH = 40:60 |
| Flow rate | 25 mL/min |
| Detection wavelength | 254 nm |
| Column temperature | 30° C. |

$t_R$=6.968 min

LCMS m/z $(M+H)^+$: 422.2.

$^1H$ NMR (400 MHz, $CDCl_3$): δ 8.02-7.99 (m, 2H), 7.16-7.10 (m, 2H), 6.83-6.73 (m, 3H), 4.01 (d, J=14.0 Hz, 1H), 3.35 (d, J=14.0 Hz, 1H), 3.33 (s, 3H), 3.00-2.91 (m, 3H), 2.67-2.55 (m, 2H), 2.40-2.19 (m, 3H), 1.98-1.81 (m, 4H), 1.55-1.46 (m, 4H).

Embodiment 1-B: Preparation of (6bS,10aR)-8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxalin-2(3H)-one (Compound 1-B)

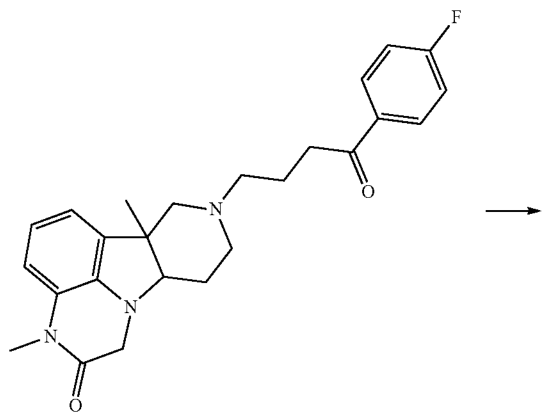

1

-continued

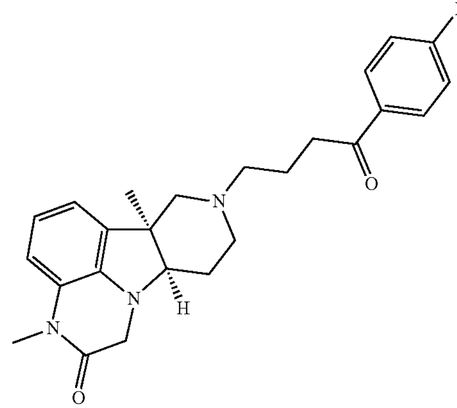

1-B

Compound 1 (1.6 g) was chiral resolved to obtain compound 1-B (467.8 mg). Chiral resolution conditions are as follows:

| | |
|---|---|
| Instrument | Gilson GX-281 |
| Column type | Chiralpak IE 250 mm * 30 mm 5 μm |
| Sample volume | 1500 μL |
| Mobile phase | Hex:EtOH = 40:60 |
| Flow rate | 25 mL/min |
| Detection wavelength | 254 nm |
| Column temperature | 30° C. |

$t_R$=8.030 min.

LCMS m/z $(M+H)^+$: 422.2.

$^1H$ NMR (400 MHz, $CDCl_3$): δ 8.02-7.99 (m, 2H), 7.16-7.10 (m, 2H), 6.84-6.73 (m, 3H), 4.01 (d, J=14.0 Hz, 1H), 3.36 (d, J=14.0 Hz, 1H), 3.33 (s, 3H), 3.00-2.91 (m, 3H), 2.67-2.55 (m, 2H), 2.40-2.19 (m, 3H), 1.98-1.81 (m, 4H), 1.55-1.46 (m, 4H).

Embodiment 2: Preparation of 6b-ethyl-8-(4-(4-fluorophenyl)-4-oxobutyl)-3-methyl-6b,7,8,9,10,10a-hexahydro-1H-pyrido[3',4':4,5]pyrrolo[1,2,3-de]quinoxalin-2(3H)-one (Compound 2)

Step 1: Preparation of 6b-ethyl-8-(2,2,2-trifluoroacetyl)-6b,7,8,9,10,10a-hexahydro-1H-pyrido[3',4':4,5]pyrrolo[1,2,3-de]quinoxalin-2(3H)-one (Intermediate 2-2)

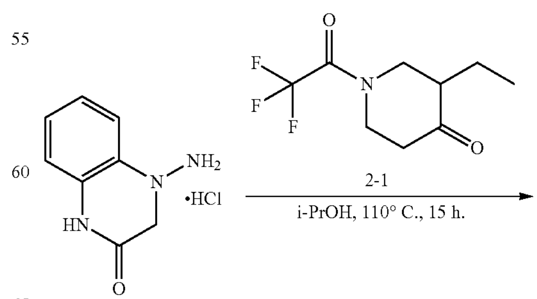

1-3

-continued

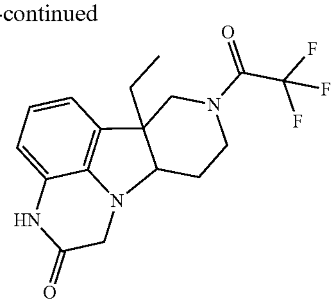

2-2

Intermediate 2-1 (800 mg, 3.58 mmol) and intermediate 1-3 (1.5 g, 9.2 mmol) were dissolved in isopropanol (50 mL), and the reaction mixture was reacted at 110° C. for 15 hours. The reaction mixture was cooled to room temperature and evaporated by rotary evaporation under reduced pressure. The product was separated and purified by column chromatography (EA/PE=1/2) to obtain intermediate 2-2, yellow solid 360 mg, yield: 28.4%. LCMS m/z $(M+H)^+$: 354.2.

Step 2: Preparation of 6b-ethyl-3-methyl-8-(2,2,2-trifluoroacetyl)-6b,7,8,9,10,10a-hexahydro-1H-pyrido[3',4':4,5]pyrrolo[1,2,3-de]quinoxalin-2(3H)-one (Intermediate 2-3)

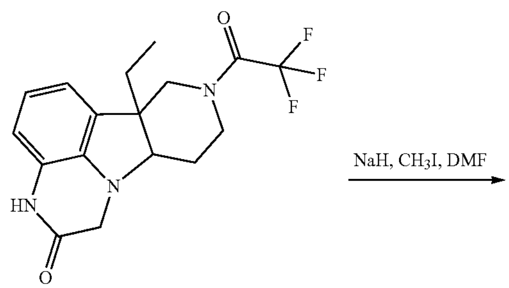

2-2

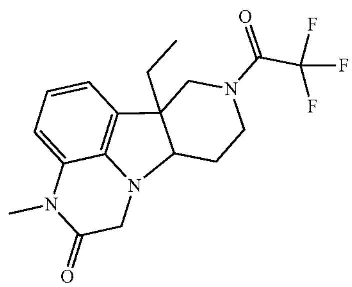

2-3

NaH (68 mg, 1.70 mmol) was added to a solution of intermediate 2-2 (400 mg, 1.13 mmol) in DMF (15 mL) in an ice bath, and the reaction was carried out for 30 minutes by keeping the temperature, then $CH_3I$ (241 mg, 1.70 mmol) was added to the reaction system, and after the addition, the reaction mixture was transferred to room temperature and reacted for 16 hours. The reaction mixture was quenched with water (15 mL) in an ice bath, and the reaction mixture was extracted with ethyl acetate (20 mL×3). The organic phases were combined, dried over anhydrous sodium sulfate, filtered, and the filtrate was concentrated under reduced pressure, and the crude product was subjected to column chromatography (PE/EA=5:1, v/v) to obtain intermediate 2-3, yellow solid 200 mg, yield: 48%. LCMS m/z $(M+H)^+$: 368.3.

Step 3: Preparation of 6b-ethyl-3-methyl-6b,7,8,9,10,10a-hexahydro-1H-pyrido[3',4':4,5]pyrrolo[1,2,3-de]quinoxalin-2(3H)-one (Intermediate 2-4)

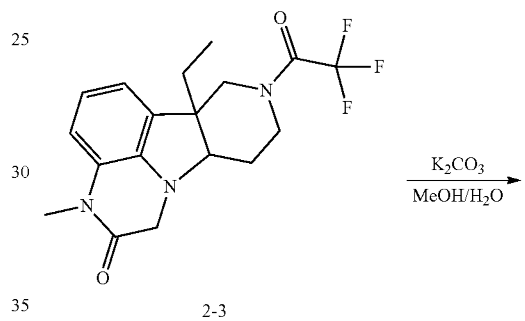

2-3

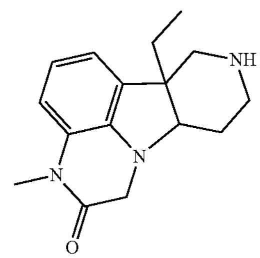

2-4

$K_2CO_3$ (150 mg, 1.09 mmol) was added to a solution of intermediate 2-3 (200 mg, 0.54 mmol) in $MeOH/H_2O$ (10 mL/1 mL) at room temperature, and after the addition, the reaction mixture was reacted at 70° C. for 4 hours. The reaction mixture was cooled to room temperature, and water (10 mL) was added thereto, then the mixture was extracted with dichloromethane (20 mL×3), and the combined organic phases were dried over anhydrous sodium sulfate, filtered, and the filtrate was evaporated by rotary evaporation under reduced pressure to obtain the crude product. The crude product was subjected to column chromatography (DCM/MeOH=20:1, v/v) to obtain intermediate 2-4, yellow oil 120 mg, yield: 65%. LCMS m/z $(M+H)^+$: 272.2.

Step 4: Preparation of 6b-ethyl-8-(4-(4-fluorophenyl)-4-oxobutyl)-3-methyl-6b,7,8,9,10,10a-hexahydro-1H-pyrido[3',4':4,5]pyrrolo[1,2,3-de]quinoxalin-2(3H)-one (Compound 2)

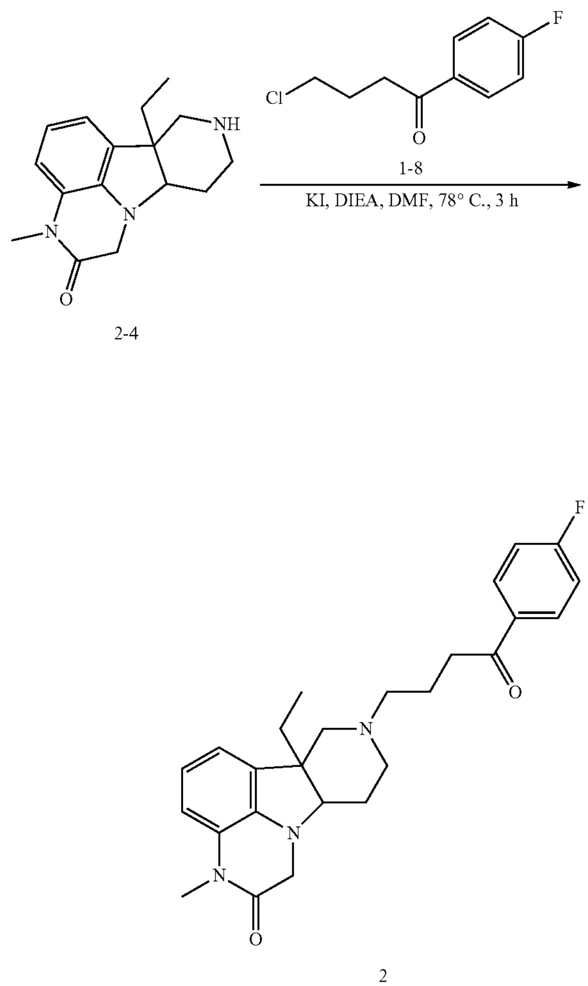

1-8

2-4

2

A solution of intermediate 2-4 (100 mg, 0.37 mmol), intermediate 1-8 (590 mg, 2.95 mmol), KI (245 mg, 1.48 mmol) and DIEA (190 mg, 1.48 mmol) in DMF (10 mL) was stirred at 78° C. for 16 hours, and the reaction mixture was cooled to room temperature and water (10 mL) was added thereto. The mixture was extracted with ethyl acetate (20 mL×3), and the combined organic phases were dried over anhydrous sodium sulfate, filtered, and the filtrate was evaporated by rotary evaporation under reduced pressure to obtain the crude product. The crude product was separated and purified by preparative liquid phase ($CH_3CN$:$H_2O$ (0.1% $NH_4HCO_3$)=40-80%, UV: 214 nm, flow rate: 15 mL/min) to obtain compound 2, 45.0 mg, yield: 23%. LCMS m/z $(M+H)^+$: 436.2.

$^1H$ NMR ($CDCl_3$, 400 MHz): δ 8.03-7.95 (m, 2H), 7.13 (t, J=8.4 Hz, 2H), 6.83-6.74 (m, 2H), 6.74-6.68 (m, 1H), 4.01 (d, J=14.0 Hz, 1H), 3.37 (d, J=14.4 Hz, 1H), 3.32 (s, 3H), 3.10-3.04 (m, 1H), 2.98 (t, J=7.2 Hz, 2H), 2.69-2.51 (m, 2H), 2.43-2.31 (m, 1H), 2.30-2.15 (m, 2H), 2.11-1.99 (m, 1H), 1.97-1.76 (m, 6H), 0.88 (t, J=7.6 Hz, 3H).

Embodiment 3: Preparation of 3-ethyl-8-(4-(4-fluorophenyl)-4-oxobutyl)-6b-methyl-6b,7,8,9,10,10a-hexahydro-1H-pyrido[3',4':4,5]pyrrolo[1,2,3-de]quinoxalin-2(3H)-one (Compound 3)

Step 1: Preparation of 3-ethyl-6b-methyl-8-(2,2,2-trifluoroacetyl)-6b,7,8,9,10,10a-hexahydro-1H-pyrido[3',4',4,5]pyrrolo[1,2,3-de]quinoxalin-2(3H)-one (Intermediate 3-1)

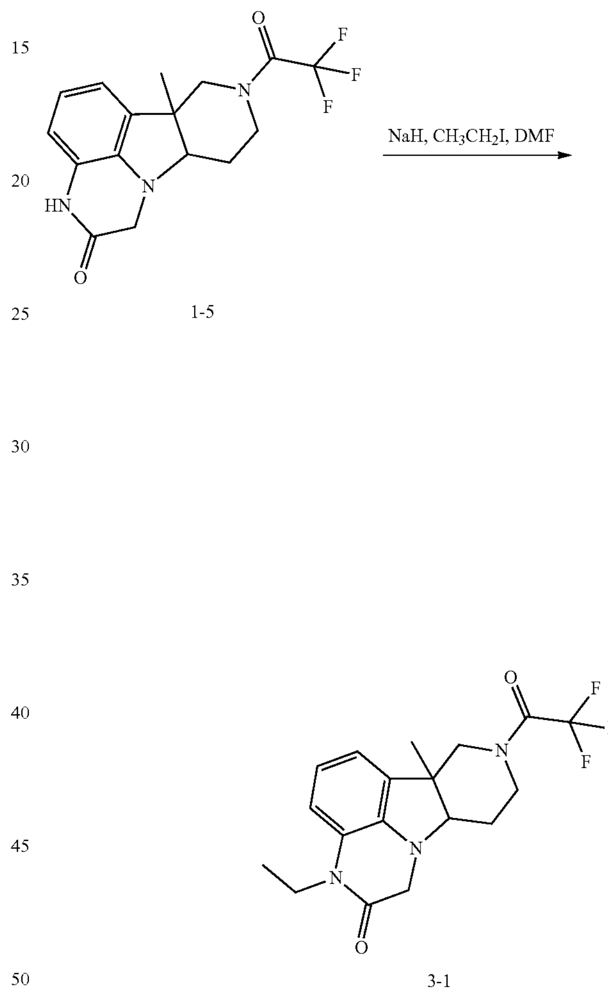

1-5

3-1

Sodium hydride (28 mg, 0.71 mmol) was added to a solution of intermediate 1-5 (0.2 g, 0.59 mmol, prepared according to the method described in step 3 of Embodiment 1) in DMF (10 mL) in an ice bath, and the reaction was carried out for 30 minutes by keeping the temperature. Iodomethane (148 mg, 0.89 mmol) was added to the mixture, and after addition, the reaction mixture was transferred to room temperature and stirred for 1 hour, then the reaction mixture was placed back in an ice bath, quenched by adding water (5 mL), extracted with ethyl acetate (10 mL×3), and the combined organic phases were dried over sodium sulfate and concentrated. The crude product was purified by column chromatography (DCM/MeOH=20/1) to obtain intermediate 3-1, yellow solid 150 mg, yield: 69%. LCMS m/z $(M+H)^+$: 368.2.

Step 2: Preparation of 3-ethyl-6b-methyl-6b,7,8,9,10,10a-hexahydro-1H-pyrido[3',4':4,5]pyrrolo[1,2,3-de]quinoxalin-2(3H)-one (Intermediate 3-2)

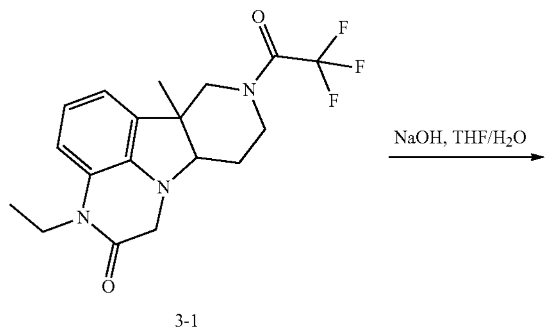

3-1

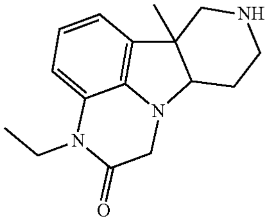

3-2

Sodium hydroxide (32 mg, 0.82 mmol) was added to a solution of intermediate 3-1 (150 mg, 0.41 mmol) in tetrahydrofuran/water (10 mL/2 mL), and after addition, the reaction mixture was reacted at 40° C. for 2 hours, then the mixture was evaporated to dryness by rotary evaporation under reduced pressure. The crude product was separated and purified by column chromatography (DCM/MeOH/$NH_3H_2O$=100/10/1) to obtain intermediate 3-2, yellow oil 91 mg, yield: 82%. LCMS m/z $(M+H)^+$: 272.2.

Step 3: Preparation of 3-ethyl-8-(4-(4-fluorophenyl)-4-oxobutyl)-6b-methyl-6b,7,8,9,10,10a-hexahydro-1H-pyrido[3',4':4,5]pyrrolo[1,2,3-de]quinoxalin-2(3H)-one (Compound 3)

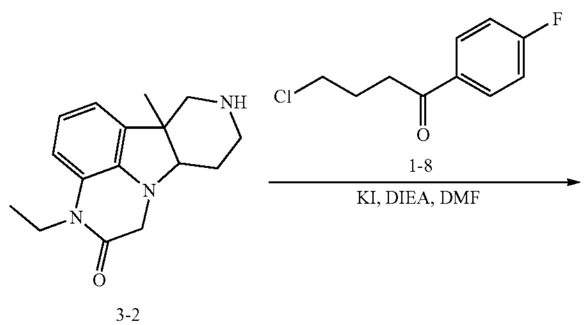

3-2 1-8

-continued

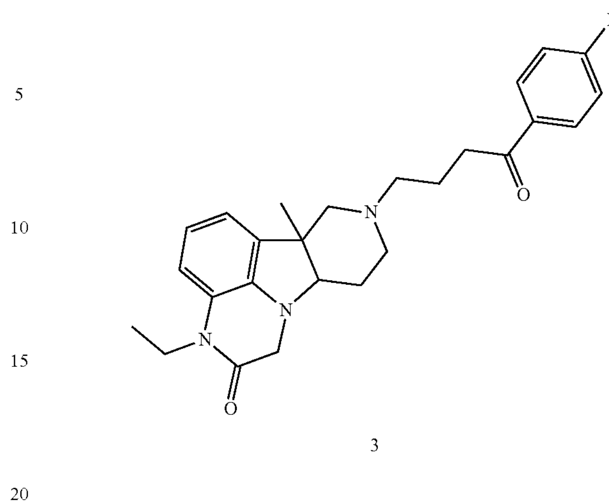

3

Intermediate 1-8 (136 mg, 0.68 mmol), potassium iodide (10 mg) and N,N-diisopropylethylamine (88 mg, 0.68 mmol) were added to a solution of intermediate 3-2 (91 mg, 0.34 mmol) in DMF (10 mL), and after addition, the reaction mixture was reacted at 78° C. for 3 hours. The reaction mixture was cooled to room temperature and concentrated to obtain the crude product, and the crude product was separated and purified by preparative liquid phase ($CH_3CN:H_2O$ (0.1% $NH_4HCO_3$)=10-60%, UV:214 nm, flow rate: 15 mL/min) to obtain compound 3, 42.3 mg, yield: 28%. LCMS m/z $(M+H)^+$: 436.2.

$^1H$ NMR ($CDCl_3$, 400 MHz): δ 8.04-8.01 (m, 2H), 7.17-7.13 (m, 2H), 6.86-6.76 (m, 3H), 4.06-3.98 (m, 2H), 3.90-3.84 (m, 1H), 3.37 (d, J=14.4 Hz, 1H), 3.03-2.99 (m, 2H), 2.91 (s, 1H), 2.68-2.56 (m, 2H), 2.43-2.21 (m, 3H), 1.97-1.84 (m, 5H), 1.47 (s, 3H), 1.30-1.27 (m, 3H).

Embodiment 4: Preparation of 8-(4-(4-fluorophenyl)-4-oxobutyl)-1,1,3,6b-tetramethyl-6b,7,8,9,10,10a-hexahydro-1H-pyrido[3',4':4,5]pyrrolo[1,2,3-de]quinoxalin-2(3H)-one (Compound 4)

Step 1: Preparation of 3,6b-dimethyl-2-oxo-2,3,6b,9,10,10a-hexahydro-1H-pyrido[3',4':4,5]pyrrolo[1,2,3-de]quinoxaline-8(7H)-carboxylate (Intermediate 4-1)

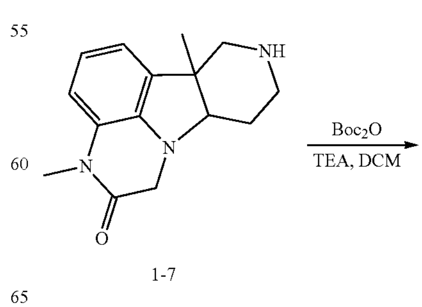

1-7

-continued

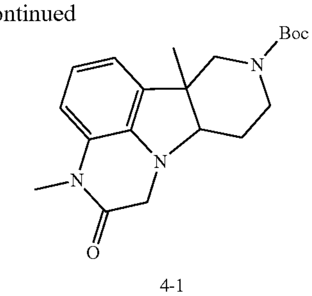

4-1

Triethylamine (1.3 g, 13.2 mmol) and di-tert-butyl dicarbonate (4.3 g, 19.8 mmol) were added sequentially to a solution of intermediate 1-7 (1.2 g, 4.6 mmol, prepared according to the method described in step 5 of Embodiment 1) in DCM (20 mL), and the mixture was stirred at room temperature for 2 hours, then the mixture was quenched by adding water (15 mL) and the phases were separated to obtain the organic phase. The organic phase was dried and concentrated to obtain a crude product and the crude product was separated and purified by column chromatography (EA/PE=1/3) to obtain intermediate 4-1, white solid 1.6 g, yield: 68%. LCMS m/z (M−56+H)$^+$: 302.2.

Step 2: Preparation of 1,1,3,6b-tetramethyl-2-oxo-2,3,6b,9,10,10a-hexahydro-1H-pyrido[3',4': 4,5]pyrrolo[1,2,3-de]quinoxaline-8(7H)-carboxylate (Intermediate 4-2)

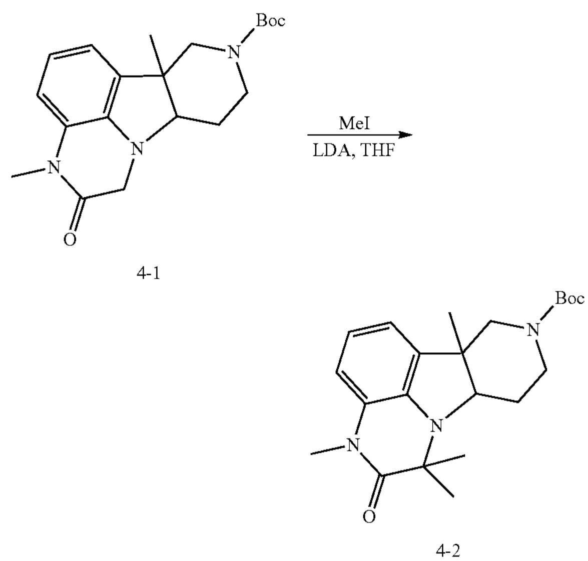

4-1

4-2

Intermediate 4-1 (0.66 g, 1.85 mmol) was dissolved in tetrahydrofuran (20 mL), and the mixture was placed in a low-temperature reactor at −78° C. LDA (lithium diisopropyl amine, 2.0 M, 3.7 mL, 7.4 mmol) was added slowly in dropwise under argon protection, and after the dropwise addition, the reaction was carried out for 1 hour by keeping the temperature. Then iodomethane (2.1 g, 14.8 mmol) was added slowly in dropwise, and after addition, the reaction was carried out for 2 hours by keeping the temperature. The reaction mixture was transferred to room temperature and quenched by adding water (20 mL), and the reaction mixture was extracted with ethyl acetate (15 mL×3). Then the organic phases were dried and concentrated, and the obtained crude product was separated and purified by column chromatography (EA/PE=1/2) to obtain intermediate 4-2, yellow oil 410 mg, yield: 58%. LCMS m/z (M+H)$^+$: 386.2.

Step 3: Preparation of 1,1,3,6b-tetramethyl-6b,7,8,9,10,10a-hexahydro-1H-pyrido[3',4':4,5]pyrrolo[1,2,3-de]quinoxalin-2(3H)-one (Intermediate 4-3)

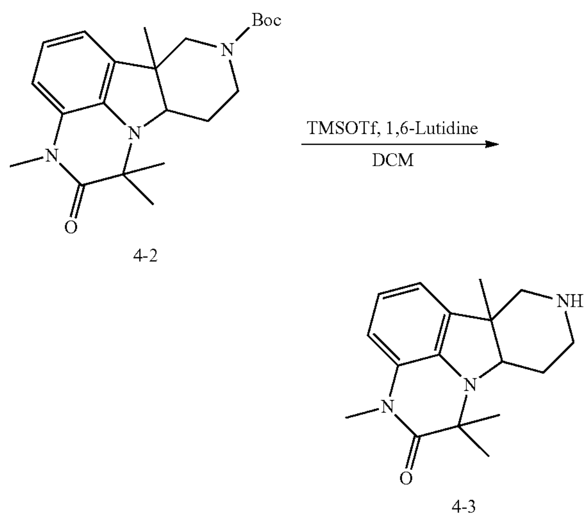 [SMILES: CN1C(=O)C(C)(C)N2c3c1cccc3C1(C)CN(C(=O)OC(C)(C)C)CCC21 ; CN1C(=O)C(C)(C)N2c3c1cccc3C1(C)CNCCC21]

4-2

4-3

TMSOTf (trimethylsilyl trifluoromethanesulfonate, 380 mg, 1.71 mmol) was added to a solution of intermediate 4-2 (0.44 g, 1.14 mmol) and 1,6-Lutidine (0.24 g, 2.28 mmol) in DCM (50 mL) in an ice bath, and the reaction was carried out for 30 minutes by keeping the temperature. Then the reaction mixture was quenched with aqueous ammonium chloride (15 mL). After liquid separation, the organic phase was dried and concentrated to obtain a crude product. The product was separated and purified by column chromatography (DCM/MeOH=10/1) to obtain intermediate 4-3, yellow oil 200 mg, yield: 61%. LCMS m/z (M+H)$^+$: 286.2.

Step 4: Preparation of 8-(4-(4-fluorophenyl)-4-oxobutyl)-1,1,3,6b-tetramethyl-6b,7,8,9,10,10a-hexahydro-1H-pyrido[3',4':4,5]pyrrolo[1,2,3-de]quinoxalin-2(3H)-one (Compound 4)

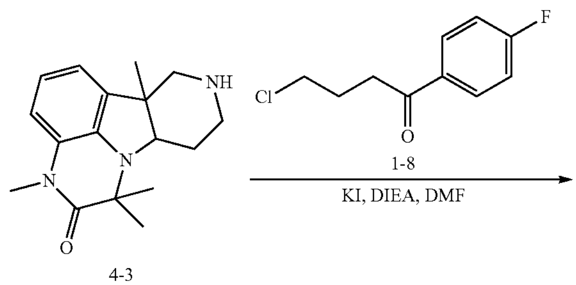

4-3

-continued

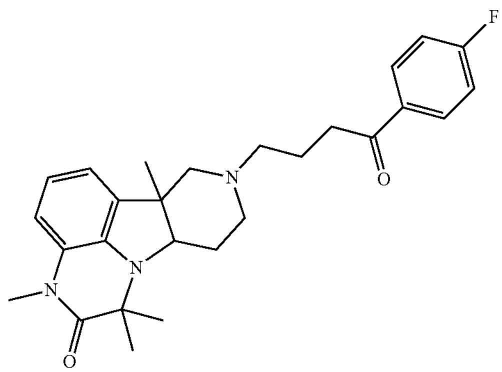

4

Intermediate 4-3 (180 mg, 0.63 mmol), intermediate 1-8 (252 mg, 1.26 mmol), potassium iodide (20 mg, 0.12 mmol) and DIEA (244 mg, 1.89 mmol) were added to DMF (10 mL) sequentially and the reaction was carried out at 78° C. for 5 hours. After the reaction was completed, the reaction mixture was concentrated under reduced pressure and directly separated and purified by preparative liquid phase ($CH_3CN$:$H_2O$ (0.1% $NH_4HCO_3$)=10-70%, UV:214 nm, flow rate: 15 mL/min) to obtain compound 4, 100 mg, yield: 38%. LCMS m/z $(M+H)^+$: 450.2.

$^1H$ NMR ($CDCl_3$, 400 MHz) δ 8.02-7.95 (m, 2H), 7.16-7.12 (m, 2H), 6.79-6.70 (m, 3H), 3.52 (s, 1H), 3.31 (s, 3H), 2.95-2.94 (m, 2H), 2.78-1.92 (m, 10H), 1.72 (s, 3H), 1.45 (s, 3H), 1.15 (s, 3H).

Embodiment 5: 8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxaline-1,2(3H)-dione (Compound 5)

Step 1: Preparation of 3,6b-dimethyl-8-(2,2,2-trifluoroacetyl)-6b,7,8,9,10,10a-hexahydro-1H-pyrido[3',4':4,5]pyrrolo[1,2,3-de]quinoxaline-1,2(3H)-dione (Intermediate 5-1)

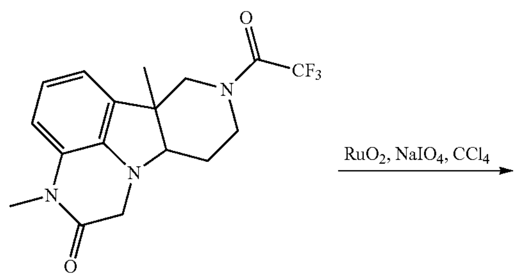

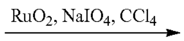

1-6

-continued

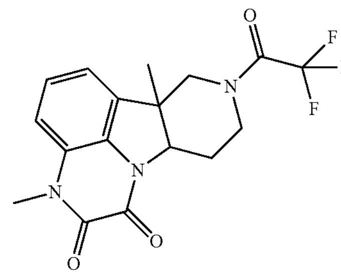

5-1

$RuO_2$ (37 mg, 0.28 mmol) and $NaIO_4$ (300 mg, 1.4 mmol) were added to a solution of intermediate 1-6 (200 mg, 0.50 mmol) in carbon tetrachloride (20 mL), and the reaction was carried out at room temperature for 48 hours, and the reaction mixture was concentrated directly to obtain the crude product. The product was subjected to column chromatography (EA/PE=1:1) to obtain intermediate 5-1, yellow solid 114 mg, yield: 54%. LCMS m/z $(M+H)^+$: 368.2.

Step 2: Preparation of 3,6b-dimethyl-6b,7,8,9,10,10a-hexahydro-1H-pyrido[3',4':4,5]pyrrolo[1,2,3-de]quinoxaline-1,2(3H)-dione (Intermediate 5-2)

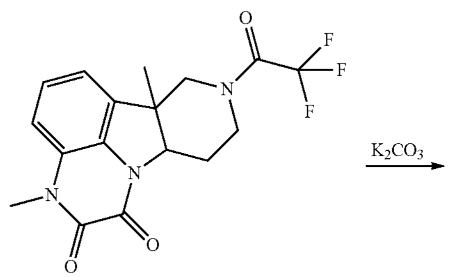

5-1

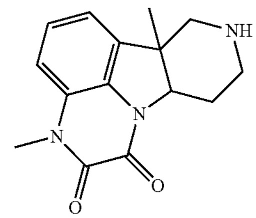

5-2

Potassium carbonate (136 mg, 0.98 mmol) was added to a solution of intermediate 5-1 (180 mg, 0.49 mmol) in methanol/water (2 mL, v/v=10/1), and the reaction mixture was reacted at 70° C. for 3 hours. After the reaction was completed, the reaction mixture was concentrated to obtain intermediate 5-2 (yellow oil, 150 mg) and the product was directly used as raw material in the next step without further purification. LCMS m/z $(M+H)^+$: 272.2.

Step 3: Preparation of 8-(4-(4-fluorophenyl)-4-oxobutyl)-3,6b-dimethyl-6b,7,8,9,10,10a-hexahydro-1H-pyrido[3',4':4,5]pyrrolo[1,2,3-de]quinoxaline-1,2(3H)-dione (Compound 5)

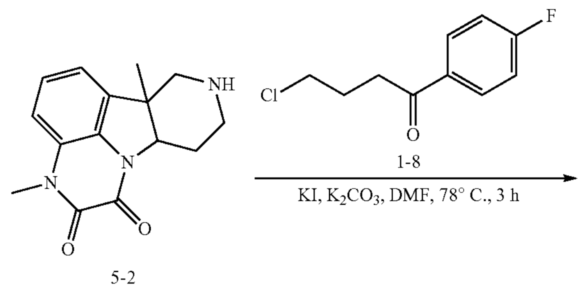

5-2

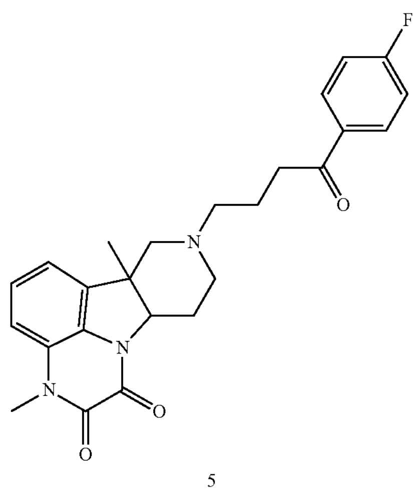

5

Intermediate 1-8 (150 mg, 0.75 mmol) and potassium carbonate (37 mg, 0.27 mmol) were added sequentially to a solution of intermediate 5-2 (150 mg, 0.55 mmol) in D1VIF (3 mL), and after addition, the reaction mixture was reacted at 78° C. for 3 hours. After the reaction was completed, the reaction mixture was concentrated directly under reduced pressure to obtain the residue, and the residue was separated and purified by preparative liquid phase ($CH_3CN$:$H_2O$ (0.1% $NH_4HCO_3$)=10-70%, UV: 214 nm, flow rate: 15 mL/min) to obtain compound 5, 35 mg, yield: 15%. LCMS m/z $(M+H)^+$: 436.2.

$^1H$ NMR ($CDCl_3$, 400 MHz): δ 8.02-7.98 (m, 2H), 7.15-7.10 (t, J=8.4 Hz, 1H), 6.59-6.56 (m, 3H), 4.32-4.29 (m, 2H), 4.32-4.29 (d, J=11.2 Hz, 2H), 3.07-2.99 (m, 5H), 2.66-2.45 (m, 5H), 2.12 (t, J=7.6 Hz, 2H), 2.03-1.97 (m, 4H).

Embodiment 6: Preparation of 8-(3-(4-fluorophenoxy)propyl)-3,6b-dimethyl-6b,7,8,9,10,10a-hexahydro-1H-pyrido[3',4':4,5]pyrrolo[1,2,3-de]quinoxalin-2(3H)-one (Compound 6)

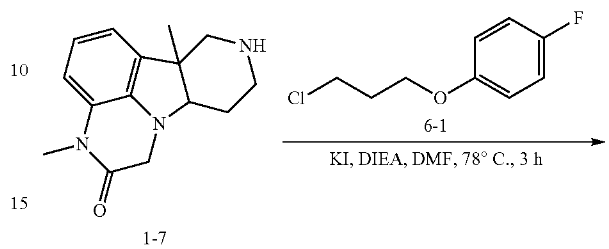

1-7

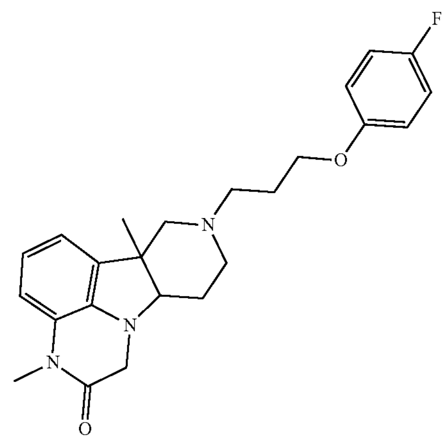

6

Intermediate 1-7 (2.0 g, 7.78 mmol, prepared according to the method described in step 5 of Embodiment 1), intermediate 6-1 (2.9 g, 15.56 mmol), potassium iodide (2.0 g, 15.56 mmol) and DIEA (2.0 g, 15.56 mmol) were added sequentially to DMF (40 mL) and the reaction was carried out at 78° C. for 3 hours. After the reaction was completed, the reaction mixture was concentrated directly, and the obtained crude product was separated and purified by preparative liquid phase to obtain compound 6, 1.5 g, yield: 47%. LCMS m/z $(M+H)^+$: 410.2.

$^1H$ NMR ($CDCl_3$, 400 MHz): δ 6.98-6.93 (m, 2H), 6.84-6.28 (m, 5H), 4.03-3.96 (m, 3H), 3.38 (s, 1H), 3.33 (s, 3H), 2.92 (s, 1H), 2.68-2.22 (m, 5H), 1.96-1.89 (m, 5H), 1.49 (s, 3H).

Embodiment 7: Preparation of 4-(3,6b-dimethyl-2,3,6b,9,10,10a-hexahydro-1H-pyrido[3',4':4,5]pyrrolo[1,2,3-de]quinoxalin-8(7H)-yl)-1-(4-fluorophenyl)butan-1-one (Compound 7)

Step 1: Preparation of 3,6b-dimethyl-2,3,6b,7,8,9,10,10a-octahydro-1H-pyrido[3',4':4,5]pyrrolo[1,2,3-de]quinoxaline (Intermediate 7-1)

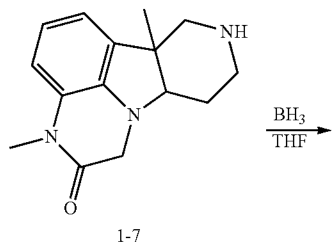

1-7

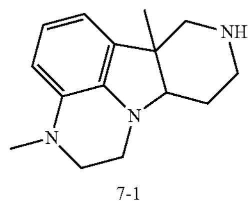

7-1

Intermediate 1-7 (0.2 g, 0.78 mmol) was dissolved in THF (10 mL), and a solution of borane (at a concentration of 1 M) in tetrahydrofuran (1.56 mL, 1.56 mmol) was slowly added thereto. The reaction mixture was stirred at room temperature for 15 hours and then quenched by adding 1 N aqueous hydrochloric acid (2 mL) dropwise in an ice bath, and the quenched reaction mixture was concentrated directly and subjected to column chromatography to obtain intermediate 7-1, 80 mg, yield: 42%. LCMS m/z $(M+H)^+$: 244.2.

Step 2: Preparation of 4-(3,6b-dimethyl-2,3,6b,9,10,10a-hexahydro-1H-pyrido[3',4':4,5]pyrrolo[1,2,3-de]quinoxalin-8(7H)-yl)-1-(4-fluorophenyl)butan-1-one (Compound 7)

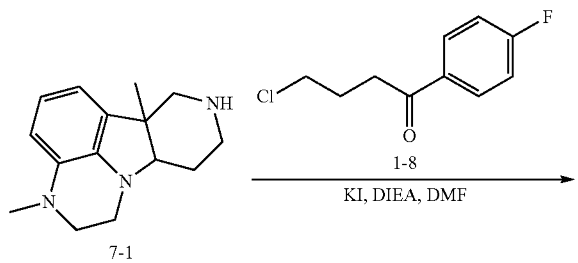

7-1

-continued

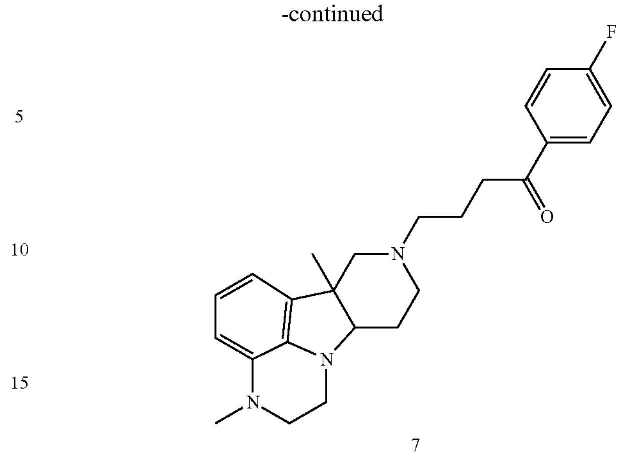

7

Intermediate 7-1 (75 mg, 0.308 mmol), intermediate 1-8 (184 mg, 0.924 mmol), potassium iodide (101 mg, 0.616 mmol) and DIEA (119 mg, 0.924 mmol) were added to DMF (3 mL), and the reaction mixture was reacted at 78° C. for 3 hours. The reaction mixture was cooled to room temperature and then concentrated directly to remove DMIF. The product was separated and purified by preparative liquid phase ($CH_3CN:H_2O$ (0.1% $NH_4HCO_3$)=10-70%, UV: 214 nm, flow rate: 15 mL/min) to obtain a target compound 7, 32 mg, yield: 25%. LCMS m/z $(M+H)^+$: 407.9.

$^1H$ NMR ($CDCl_3$, 400 MHz): δ 8.06-8.03 (m, 2H), 7.19-7.15 (m, 2H), 6.73-6.71 (m, 1H), 6.49-6.44 (m, 2H), 3.67-3.61 (m, 1H), 3.36-3.27 (m, 2H), 3.07-3.04 (m, 2H), 2.90-2.83 (m, 5H), 2.71-2.07 (m, 10H), 1.30 (s, 3H).

Comparative Embodiment 1: 8-(4-(4-fluorophenyl)-4-oxobutyl)-3-methyl-6b,7,8,9,10,10a-hexahydro-1H-pyrido[3',4':4,5]pyrrolo[1,2,3-de]quinoxalin-2(3H)-one Step 1: Synthesis of 8-(2,2,2-trifluoroacetyl)-7,8,9,10-tetrahydro-1H-pyrido[3',4':4,5]pyrrolo[1,2,3-de]quinoxalin-2(3H)-one (Intermediate D1-2)

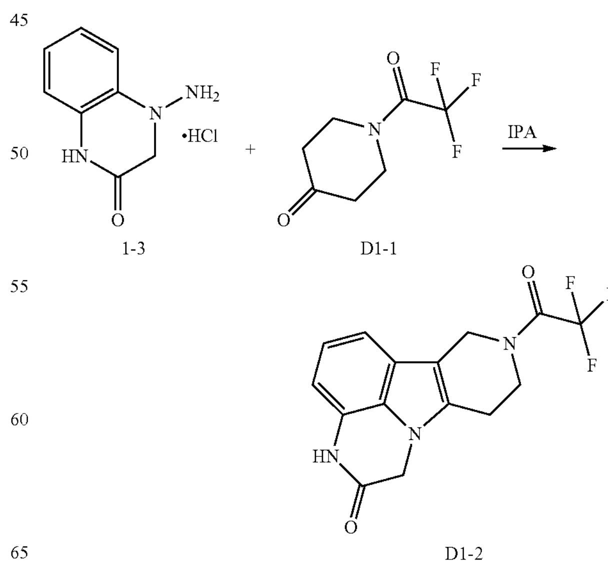

1-3 D1-1

D1-2

Intermediate 1-3 (3 g, 15 mmol), intermediate D1-1(1.8 g, 15 mmol) and isopropanol (30 mL) were added into a 100 mL single-necked bottle sequentially, and the mixture was heated to reflux and reacted overnight. After the reaction was completed, the reaction mixture was poured into ice water (5 mL), extracted with ethyl acetate (15 mL), dried over anhydrous sodium sulfate, concentrated under reduced pressure, and subjected to silica gel column chromatography (petroleum ether:ethyl acetate=2:1) to obtain intermediate D1-2, 1.8 g, yield: 30%. LCMS m/z $(M+H)^+$: 324.2.

Step 2: Synthesis of 8-(2,2,2-trifluoroacetyl)-6b,7,8,9,10,10a-hexahydro-1H-pyrido[3',4':4,5]pyrrolo[1,2,3-de]quinoxalin-2(3H)-one (Intermediate D1-3)

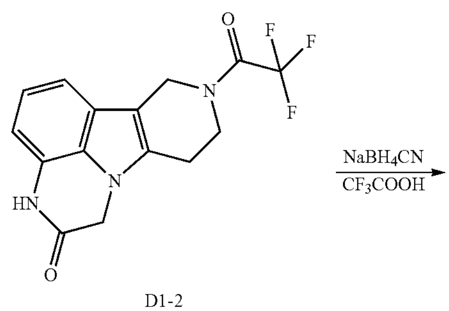

D1-2

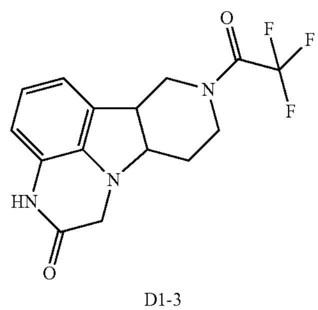

D1-3

Intermediate D1-2 (1 g, 31 mmol) was dissolved in trifluoroacetic acid (10 mL), and sodium cyanoborohydride (388 mg, 6.2 mmol) was added thereto in an ice bath, and the reaction was carried out for 2 hours in an ice bath. After the reaction was completed, the reaction mixture was poured into ice water (50 mL), then the PH was adjusted to 7, and the mixture was extracted with ethyl acetate (15 mL), dried over anhydrous sodium sulfate, concentrated to dryness under reduced pressure to obtain intermediate D1-3, 700 mg, yield: 70%.

Step 3: Synthesis of 3-methyl-8-(2,2,2-trifluoroacetyl)-6b,7,8,9,10,10a-hexahydro-1H-pyrido[3',4':4,5]pyrrolo[1,2,3-de]quinoxalin-2(3H)-one (intermediate D1-4)

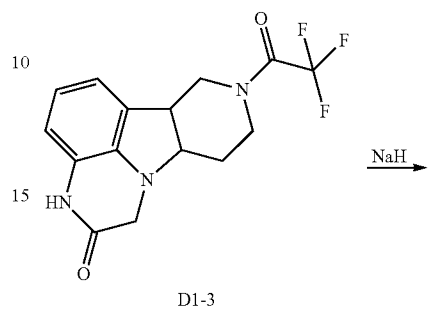

D1-3

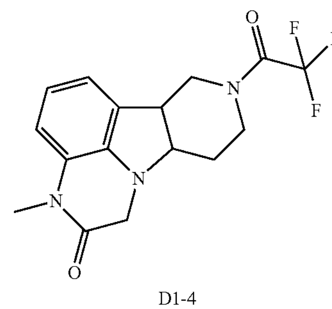

D1-4

Intermediate D1-3 (700 mg, 2.15 mmol) was dissolved in DMF (10 mL), and sodium hydride (100 mg, 2.58 mmol) and deuterated methyl iodide (340 mg, 2.37 mmol) were added thereto in an ice bath, and the reaction was carried out in an ice bath for 1 hour. After the reaction was completed, the reaction mixture was poured into ice water (5 mL), extracted with ethyl acetate (15 mL), dried over sodium sulfate, concentrated to dryness under reduced pressure to obtain intermediate D1-4, 500 mg, yield: 69%. LCMS m/z $(M+H)^+$: 340.1.

Step 4: Synthesis of 3-methyl-6b,7,8,9,10,10a-hexahydro-1H-pyrido[3',4':4,5]pyrrolo[1,2,3-de]quinoxalin-2(3H)-one (intermediate D1-5)

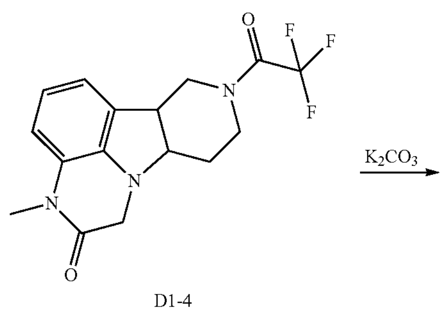

D1-4

-continued

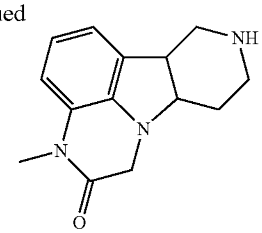

D1-5

Intermediate D1-4 (300 mg, 0.88 mmol) was dissolved in methanol (5 mL), and potassium carbonate (235 mg, 1.7 mmol) was added thereto, and the reaction was carried out at 80° C. for 2 hours. After the reaction was completed, the mixture was concentrated under reduced pressure, then water (15 mL) was added, and the mixture was extracted with dichloromethane (10 mL×3), dried over anhydrous sodium sulfate, concentrated under reduced pressure to obtain intermediate D1-5, 200 mg, yield: 93%. LCMS m/z $(M+H)^+$: 244.0.

Step 5: Synthesis of 8-(4-(4-fluorophenyl)-4-oxobutyl)-3-methyl-6b,7,8,9,10,10a-hexahydro-1H-pyrido[3',4':4,5]pyrrolo[1,2,3-de]quinoxalin-2(3H)-one

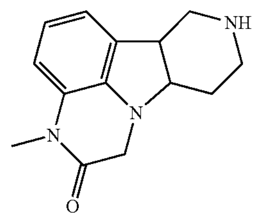

D1-5

+

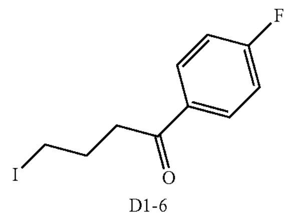

D1-6

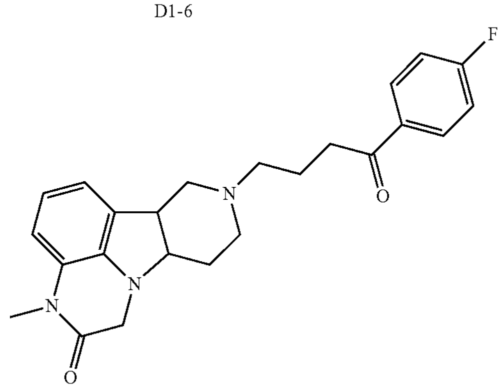

comparative embodiment 1

Intermediate D1-5 (200 mg, 0.82 mmol) and intermediate D1-6 (324 mg, 1.23 mmol) were dissolved in acetonitrile (5 mL), and cesium carbonate (400 mg, 1.23 mmol) was added thereto, and the reaction was carried out at room temperature overnight. After the reaction was completed, the mixture was filtered under reduced pressure and concentrated to dryness under reduced pressure, and the final product of comparative embodiment 1 was obtained by Pre HPLC ($MeCN:H_2O$=40:60), 56 mg, yield: 18%. LCMS m/z $(M+H)^+$: 408.2.

$^1H$ NMR (600 MHz, $CD_3OD$): δ 8.08-8.06 (m, 2H), 7.24-7.21 (m, 2H), 6.97-6.85 (m, 3H), 4.03 (d, J=13.8 Hz, 1H), 3.47-3.38 (m, 4H), 3.32 (s, 3H), 3.22-3.20 (m, 1H), 3.13-3.08 (m, 2H), 2.87-2.80 (m, 3H), 2.30-2.20 (m, 2H), 2.11-2.05 (m, 3H).

Comparative Embodiment 2: 1-(4-fluorophenyl)-4-(3-methyl-2,3,6b,9,10,10a-hexahydro-1H-pyrido[3',4':4,5]pyrrolo[1,2,3-de]quinoxalin-8(7H)-yl)butan-1-one

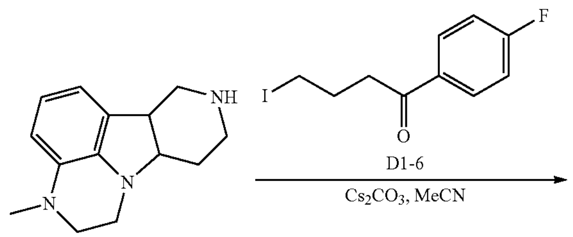

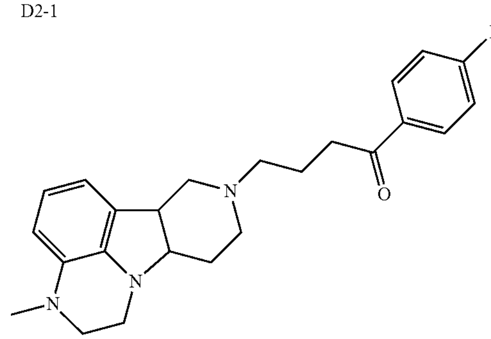

comparative embodiment 2

3-Methyl-2,3,6b,7,8,9,10,10a-octahydro-1H-pyrido[3',4':4,5]pyrrolo[1,2,3-de]quinoxaline (500 mg, 2.18 mmol) was dissolved in 15 mL of anhydrous acetonitrile, then cesium carbonate (1.42 g, 4.36 mmol) and 1-(4-fluorophenyl)-4-iodobutan-1-one (955.27 mg, 3.27 mmol) were added thereto, and the reaction mixture was stirred at room temperature for 4 hours. The product was monitored by LCMS for generation. The reaction mixture was dissolved in water (50 mL) and extracted twice with ethyl acetate (50 mL×2), and the collected organic phases were dried over anhydrous sodium sulfate, filtered and concentrated, and the crude product was purified by a rapid preparation column machine (petroleum ether:ethyl acetate=10:1-1:4) to obtain comparative embodiment 2 (600 mg, 2.18 mmol, yield: 69.93%).

$^1H$ NMR (600 MHz, DMSO-$d_6$) δ: 8.06-8.01 (m, 2H), 7.33 (t, J=9.0 Hz, 2H), 6.49 (t, J=7.2 Hz, 1H), 6.39 (d, J=7.2 Hz, 1H), 6.31 (d, J=7.8 Hz, 1H), 3.45-3.22 (m, 3H), 3.03 (br. s., 1H), 2.98 (t, J=6.6 Hz, 2H), 2.90-2.84 (m, 1H), 2.77 (s, 3H), 2.73-2.68 (m, 1H), 2.65 (dt, J=9.6, 3.0 Hz, 1H), 2.55-2.50 (m, 1H), 2.32-2.20 (m, 2H), 2.06 (dt, J=11.4, 2.4 Hz, 1H), 1.85-1.76 (m, 3H), 1.73 (t, J=10.8 Hz, 1H), 1.67-1.59 (m, 1H).

BIOLOGICAL TEST EXAMPLES

The following ITI-007 of the present disclosure is shown below, and the ITI-007 was prepared according to the method of Example 261 of Patent PCT/US2000/016498,

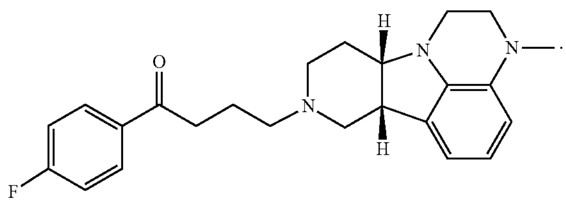 [SMILES: CN1CCN2c3c(cccc31)[C@@H]1CN(CCCC(=O)c3ccc(F)cc3)CC[C@@H]12]

The following comparative embodiment 1-A of the present disclosure is shown below, and the comparative embodiment 1-A was prepared according to the method of Scheme 1 of paragraph [0339] in the specification of patent PCT/US2017/015178,

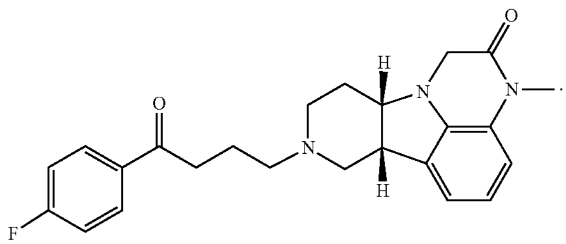 [SMILES: CN1C(=O)CN2c3c(cccc31)[C@@H]1CN(CCCC(=O)c3ccc(F)cc3)CC[C@@H]12]

Test Example 1: Functional Activity Test of Each Compound on Receptor (Cryopreservation Cells)

1. Materials and Instruments

Cells

| Cell name | Supplier: |
|---|---|
| CHO-K1/D2L/Gα15 | Genscript Biotech Co., Ltd. |
| CHO-K1/5HT2A | PerkinElmer Co., Ltd. |

Experimental Reagents and Consumables

| Reagents | Supplier | Model |
|---|---|---|
| HBSS | Gibco | 14175095 |
| HEPES | Gibco | 15630080 |
| Fluo4 Direct Calcium Assay kit | Invitrogen | F10471 |
| Advanced DMEM/F-12 | Gibco | 12634010 |
| FBS | Gibco | 10099141 |
| L-Glutamine -200 mM (100X) | Invitrogen | 25030081 |
| Ham's F-12 | Gibco | C11765500BT |
| Dialyzed FBS | Biological Industries | 04-011-1A |
| DMSO | Sigma | D8418 |
| 384-well Poly-D-Lysine plate | Greiner | 781946 |
| 384-well PP microplate, V-Form | Greiner | 781280 |
| FLIPR Pipette Tips | Molecular Device | 9000-0764 |

Instruments

| Name | Supplier |
|---|---|
| Cell counter | Countstar |
| FLIPR | Molecular Device |
| Centrifuge | Cence |
| Micro-liquid dispenser (pL) | Tecan |

Test Drugs

| Name | Supplier | Model |
|---|---|---|
| Dopamine | Sigma | H8502 |
| Serotonin | Sigma | H9523 |
| Spiperone | Targetmol | T0280 |
| Ketanserin | Targetmol | T1066 |

2. Experimental Method

Day 1: Cell Plating (1) Cells was taken out from a liquid nitrogen tank, and the tube cap was loosened and inverted to make the liquid nitrogen flow out of the tube, then the cryopreservation tube was tightened.

(2) The cryopreservation tube was shaken rapidly at 37° C. After all the ice had melted, the surface of the cryopreservation tube was wiped with 75% alcohol and placed in the biosafety cabinet.

(3) The cell suspension was transferred into a 50 mL centrifuge tube with 10 mL preheated growth medium (without screening antibiotics) added in advance.

(4) The tube was centrifuged at 1000 rpm for 5 minutes.

(5) The supernatant was discarded, and 8 mL of growth medium (without screening antibiotics) was added and blown gently. 20 μL cell suspension was taken out and counted by cell counter.

(6) Dilution according to the specified conditions: $1\times10^6$ cells/mL, 20 μL cell suspension was added into each well of the cell plate, and finally the concentration of each well is 20,000 cells/well sequentially.

(7) The cell plate was cultured in an incubator with 5% $CO_2$ and at 37° C. for 16-24 hours.

Day 2: Experimental Detection

Preparation of Detection Reagent:

(1) Preparation of 250 mM probenecid solution: 1 mL experimental buffer was added into a tube containing 77 mg powder, and the powder was dissolved by vortex oscillation.

(2) Preparation of 2× fluorescent probe solution: A bottle of fluorescent probe dry powder was taken out to balance to room temperature, and 10 mL of experimental buffer solution and 200 μL of 250 mM probenecid solution were added thereto, and the bottle was scrolled and let stand for 5 minutes to ensure complete dissolution, and then the bottle was scrolled again.

Experimental Steps:

(1) Preparation of Compound a) Preparation of agonist compound plate (test of $EC_{80}$): Dopamine and Serotonin were diluted 3-fold in a compound plate (Greiner-781280) at 10 concentration points, with an initial concentration of 1.2 μM, 30 μL per well, and DMSO concentration was not higher than 3%.

b) Preparation of the plate of antagonist-positive compound and the compound to be tested: The compound to be tested was diluted 3-fold at 10 concentration points using experimental buffer in the compound plate (Greiner-781280), with an initial concentration of 3 μM and 30 μL per well; the antagonistic positive compounds (Spiperone and Ketanserin) were diluted 3-fold at 10 concentration points using experimental buffer, with an initial concentration of 1 μM and 30 μL per well. DMSO concentration was not higher than 3%.

(2) Cell preparation: Cells was taken out from the incubator, and 20 μL of prepared 2× fluorescent probe solution was added thereto, incubated at 37° C. for 50 minutes, then equilibrated at room temperature for 10 minutes.

(3) Test of Agonist $EC_{80}$ a) The cell plate and agonist compound plate were put into the instrument, and the program of reading the plate was run.

b) 10 μL was transferred from the agonist compound plate to the cell plate, and fluorescence signal was read.

c) The $EC_{80}$ of agonist was calculated using Screenworks software and $6\times EC_{80}$ concentration was prepared for later use.

(4) $EC_{50}$ and $IC_{50}$ Test of the Compound a) The cell plate and plate of compound to be tested were put into the instrument, and the program of reading the plate was run.

b) 10 μL was transferred from the plate of compound to be tested to the cell plate, and fluorescence signal was read.

c) Then, the plate of $6\times EC_{80}$ agonist was placed, and 10 μL was transferred to the cell plate, and fluorescence signal was read.

d) The "Max-Min" value from 1 to the maximum number of times was exported as the original data for analysis, and the $EC_{50}$ and $IC_{50}$ values of the compound were calculated.

3. Experimental Results: Specific Results are Shown in Table 1

TABLE 1

Test results of in vitro functional activity of each compound

| Number of the embodiment | $D_2$ $IC_{50}$ (nM) | 5-$HT_{2A}$ $IC_{50}$ (nM) | $D_2$/5-$HT_{2A}$ ratio |
|---|---|---|---|
| Embodiment 1 | 661.58 | 50.54 | 13.09 |
| ITI-007 | 568.91 | 119.7 | 4.75 |

4. Experimental Conclusion

The current study found that high activity of 5-HT2A receptor can improve the clinical efficacy of atypical and typical antipsychotics; in addition, high selectivity to D2/5-HT2A (the higher the ratio of D2/5-HT2A, the higher the selectivity) can reduce the possibility of inducing EPS response, which is also an important design goal for anti-schizophrenic drugs.

According to the results in above Table 1, the compounds of the present disclosure has a relatively good functional activity to 5-HT2A and/or D2, and the ratio of D2/5-HT2A is higher. The results indicate that the compound of the present disclosure has good therapeutic effect on schizophrenia and can reduce the possibility of inducing EPS.

Test Example 2: Functional Detection Experiment of 5-$HT_{2A}$ Receptor (Cultured Cells)

1. Experimental Purpose

The antagonistic effect of the compound of the present disclosure on the 5-HT2A receptor was detected by a calcium influx assay at the cellular level.

2. Experimental Scheme 2.1 Experimental Materials (1) Test compounds: compounds of the embodiments of the present disclosure, self-made.

(2) Control compound: serotonin hydrochloride 5-hydroxytryptamine (Sigma, H9523), Ketanserin (Targetmol, T1066).

(3) Stable cell line:

| Cell name | Growth medium | Cryopreservation medium | Plate-laying medium |
|---|---|---|---|
| CHO-K1/5-HT2A (PerkinElmer) | Advanced DMEM/F12, 1% Dialyzed FBS, 4 mM L-Glutamine, 0.4 mg/ml Geneticin | Advanced DMEM/F12, 1% Dialyzed FBS, 4 mM L-Glutamine, 10% DMSO | Advanced DMEM/F12, 1% Dialyzed FBS, 4 mM L-Glutamine |

(4) Experimental reagents

| Reagent name | Brand | Article number |
|---|---|---|
| DMSO | Sigma | D8418 |
| Fluo-4 Direct Calcium Assay Kit | Invitrogen | F10471 |
| HBSS | Gibco | 14175103 |
| HEPES | Gibco | 15630080 |
| DMEM | Gibco | C11965500CP |
| Advanced DMEM/F12, | Gibco | 12634010 |
| Ham's F12 | Gibco | C11965500CP |
| FBS | Invitrogen | 10099141 |
| Dialyzed FBS | Biological Industries | 04-011-1A |
| Zeocin | Invitrogen | R25001 |
| Puromycin | Gibco | A11138-03 |
| Geneticin | Gibco | 10131-027 |
| L-Glutamine | Invitrogen | 25030081 |
| Penicillin-Streptomycin (PS-100X) | Gibco | 15140122 |
| PBS | Gibco | C10010500BT |
| 0.05% Trypsin-EDTA | Gibco | 25300062 |

(5) Experimental consumables:

| Consumable Name | Brand | Article number |
|---|---|---|
| Cell counting plate | Countstar | IC1000 |
| Poly-D-Lysine coated 384 well plate | Greiner | 781946 |
| 384-well-PP microplate, V-Form | Greiner | 781280 |
| Tera Pipette Tip Black, 384 | Molecular Device | 9000-0764 |

(6) Experimental instruments:

| Instrument name | Brand | Model |
|---|---|---|
| Electronic balance | Sartorius | SQP |
| FLIPR | Molecular Device | TETRA |
| Bravo | Agilent | Bravo |
| Cell counter | Countstar | BioTech |
| Ultrapure water meter | Millipore | IQ 7000 |
| Centrifuge | Cence | TDZ5-WS |
| Multifuge X4R Pro centrifuge | Thermo Fisher | 75009915 |

2.2. Preparation of Solution (1) Preparation of test compounds: the compounds of the embodiments of the present disclosure were respectively dissolved in DMSO to prepare 10 mM mother liquor, and the mother liquor was stored in the nitrogen cabinet for later use.

(2) Preparation of control compound: the control compound was dissolved in DMSO to prepare 10 mM mother liquor, and the mother liquor was repackaged and stored in the refrigerator at −80° C. for later use.

(3) Preparation of 250 mM probenecid solution: 1 mL experimental buffer was added into a tube containing 77 mg powder, and the powder was dissolved by vortex oscillation.

(4) Preparation of 2× fluorescent probe solution: a bottle of fluorescent probe dry powder was taken out to balance to room temperature, and 10 mL of experimental buffer solution and 200 μL of 250 mM probenecid solution were added thereto, and the mixture was scrolled and let stand for 5 minutes to ensure complete dissolution.

(5) Experimental buffer HBSS: HBSS and HEPES were mixed evenly in a ratio of 50:1, stored in a refrigerator at 4° C., and heated at 37° C. when used.

2.3. Experimental Method

Cell Resuscitation:

(1) Cells were taken out from the liquid nitrogen tank and melted in a water bath at 37° C. The surface of the cryopreservation tube was wiped with 75% alcohol and put in the biosafety cabinet.

(2) The cell suspension was transferred to a 15 mL centrifuge tube with 4 mL preheated plating medium, and the tube was centrifuged at 1000 rpm for 5 minutes.

(3) The supernatant was discarded, and 10 mL of plating medium was added and blown gently, and the mixture was transferred to a culture dish for growth. After the cells had adhered to the wall for 24 hours, they were replaced with growth medium for continuous culture.

Cell Plating:

(1) The logarithmic growth cells was taken and the cells grew to about 85%-90%. The cells were performed the following operations: cell cleaning, digestion, termination, then transferred to a 15 mL centrifuge tube, and the tube was centrifuged at room temperature at 1000 rpm for 5 minutes.

(2) The supernatant was discarded, and a certain plating medium was added and blown gently. 20 μL of cell suspension was taken out and counted.

(3) Cells were diluted to $1\times10^6$ cells/mL and 20 μL of cell suspension was added to each well of the cell plate (Greiner-781946), so that the density of each well is $2\times10^4$ cells/well.

(4) The cell plate was incubated in an incubator with 5% $CO_2$ at 37° C. for 16-24 hours.

Experimental Detection Steps:

(1) Preparation of compound a) Preparation of agonist compound plate (test $EC_{80}$): agonist was diluted in the compound plate (Greiner-781280) for 4-fold at 10 concentration points using experimental buffer, with 30 μL per well.

b) Preparation of the plate of compound to be tested and positive compound: compound to be tested and positive compound were diluted 4-fold at 10 concentration points in the compound plate (Greiner-781280) using experimental buffer, with 30 μL per well.

(2) Cell preparation: cells was taken out from the incubator, and 20 μL/well of 2× fluorescent probe solution was added, incubated at 37° C. for 50 minutes and equilibrated at room temperature for 10 minutes.

(3) $EC_{80}$ test of agonists a) The cell plate and agonist compound plate were put into the instrument, and the program was run.

b) 10 μL was transferred from the agonist compound plate to the cell plate, and fluorescence signal was read.

c) The $EC_{80}$ of agonist was calculated using Screenworks software and $6\times EC_{80}$ concentration was prepared for later use.

(4) $IC_{50}$ test of compound a) The cell plate and plate of compound to be tested were put into the instrument, and the corresponding program was run.

b) 10 μL was transferred from the plate of compound to be tested to the cell plate, and fluorescence signal was read.

c) The compound plate was taken out and $6\times EC_{80}$ agonist plate was put in. 10 μL was transferred from the $6\times EC_{80}$ agonist plate to the cell plate, and fluorescence signal was read.

d) The "Max-Min" value from 1 to the maximum number of times was exported as the original data for analysis, and the $IC_{50}$ values of the compounds were calculated.

3. Experimental Results: as Shown in Table 2

TABLE 2

Test results of functional activity of the compounds of the present disclosure on 5-HT2A receptor

| Number of embodiment | $5\text{-}HT_{2A}$ $IC_{50}$ (nM) |
|---|---|
| Embodiment 1 | 3.72 |
| Embodiment 1-A | 0.78 |
| Embodiment 1-B | 107.60 |
| Embodiment 4 | 19.69 |
| Embodiment 7 | 3.50 |
| Comparative embodiment 1 | 44.36 |
| Comparative embodiment 1-A | 9.11 |
| ITI-007 | 3.35 |

4. Experimental Conclusion

It is concluded from the above scheme that the compounds of the present disclosure have a relatively good antagonistic effect on the 5-$HT_{2A}$ receptor.

Test Example 3: Functional Activity Test of the Compounds of the Present Disclosure on $D_{2L}$, and $D_{2S}$ Receptors 1. Experimental Purpose The antagonistic effects of the compounds of the present disclosure on $D_{2L}$ and $D_{2S}$ receptors were detected by cyclic adenosine monophosphate (cAMP) detection method at cell-level.

2. Experimental Scheme 2.1 Experimental Materials (1) Test compound: compounds of the embodiment of the present disclosure, self-made.
(2) Control compound: dopamine hydrochloride (Sigma, H8502), (+)-Butaclamol hydrochloride (Sigma, D033).
(3) Stable cell line:

| Cell name | Growth medium | Cryopreservation medium |
|---|---|---|
| CHO-K1/D2L/Gα15 (GenScript) | Ham's F12, 10% FBS, 200 μg/ml Zeocin, 100 μg/ml Hygromycin B | 45% culture medium, 45% FBS, 10% DMSO |
| HEK293/$D_{2S}$ | DMEM, 10% FBS, 0.6 μg/ml puromycin | 70% DMEM, 20% FBS, 10% DMSO |

(4) Experimental reagents:

| Reagent name | Brand | Article number |
|---|---|---|
| DMEM | Gibco | C11965500CP |
| PBS | Gibco | C10010500CP |
| 0.05% Trypsin | Invitrogen | 25300062 |
| DMSO | Sigma | D8418 |
| cAMP Gi Assay Kit | Cisbio | 62AM9PEJ |
| IBMX | Sigma | I5879 |
| HBSS | Gibco | 14175103 |
| Forskolin | Sigma | F6886 |

(5) Experimental consumables:

| Consumable name | Brand | Article number |
|---|---|---|
| Cell counting plate | Countstar | IC1000 |
| T8+ Dispensehead Cassettes | HP | F0L59A |
| ProxiPlate-384 Plus, White 384-shallow well Microplate | PerkinElmer | 6008280 |
| 384-well-PP microplate, V-Form | Greiner | 781280 |
| 384 Tips/RACK | Agilent | 19133-102 |
| 96-well V bottom Storage Plate | costar | 3357 |

(6) Experimental instruments:

| Instrument name | Brand | Model |
|---|---|---|
| Electronic balance | Sartorius | SQP |
| EnVision | PerkinElmer | 2104 |
| Micro-sampling system (pL) | Tecan | D300e |
| Bravo | Agilent | Bravo |
| Cell counter | Countstar | BioTech |
| Ultrapure water meter | Millipore | IQ 7000 |
| Centrifuge | Cence | TDZ5-WS |

2.2 Preparation of Solution (1) Preparation of test compounds: the compounds of the embodiments of the present disclosure were respectively dissolved in DMSO to prepare 10 mM mother liquor, and the mother liquor was stored in the nitrogen cabinet for later use.
(2) Preparation of control compound: the control compound was dissolved in DMSO to prepare 10 mM mother liquor, and the mother liquor was repackaged and stored in the refrigerator at −80° C. for later use.
(3) IBMX was dissolved in DMSO to prepare 0.5 M stock solution and the stock solution was cryopreserved at −80° C.
(4) Forskolin was dissolved in DMSO to prepare 1 mM stock solution and the stock solution was cryopreserved at −80° C. for later use.
(5) Experimental buffer: 5× stimulation buffer was diluted to 1× with $ddH_2O$ and IBMX with a final concentration of 0.5 mM was added thereto, and the solution was mixed well for later use.

2.3 Experimental Method (Gi Antagonist Test)

(1) Preparation of compounds: the test compounds and positive control compound (+)-Butaclamol hydrochloride were diluted gradient using Bravo in the compound plate (Greiner-781280), and the initial concentration of working solution was 20 μM, and the working solution was diluted at 4-fold for 10 concentrations and centrifuged at 1000 rpm for 1 minute for later use.
(2) Cryopreserved D2L cells: cells was taken out from the liquid nitrogen tank and thaw in a water bath at 37° C., and the cell suspension was transferred to a centrifuge tube containing HBSS buffer, and centrifuged at 750 rpm for 5 minutes.

Cultured $D_{2S}$ cells: after absorbing the culture medium, the cells were washed with 3 mL PBS, sucked out, digested with 0.05% Trypsin for 3 min, terminated with equal volume of culture medium, transferred to centrifuge tube, and centrifuged at 750 rpm for 5 minutes. After absorbing the liquid, the centrifuge tube was added with a buffer solution containing HBSS and re-suspend, and centrifuged at 750 rpm for 5 minutes.

(3) The supernatant was discarded, and the precipitate was re-suspended with proper amount of experimental buffer, and 20 μL was taken for cell counting.
(4) Appropriate amount of cell suspension was removed, and the cell suspension was diluted to $2\times10^5$ cells/mL with experimental buffer, and the cell plate (PerkinElmer-6008280) was added with 5 μL/well cell suspension, and centrifuged at 1000 rpm for 1 minute.
(5) 5 μL/well was transferred to the cell plate with Bravo, and the cell plate was centrifuged at 1000 rpm for 1 minute, then the cell plate was closed and incubated at room temperature for 15 minutes.

(6) Forskolin was transferred to the cell plate with Tecan-D300e, and Dopamine hydrochloride with a final concentration of $EC_{90}$ was transferred to the cell plate.

(7) The cell plate was centrifuged at 1000 rpm for 1 minute, then sealed and incubated at room temperature for 45 minutes.

(8) Standard curve: cAMP with the stock solution concentration of 2848 nM was diluted 4-fold continuously at 8 points according to the initial maximum concentration of 712 nM, and 10 μL/well was taken out to add to the cell plate.

(9) 10 μL/well of detection solution containing cAMP-d2 and Anti-cAMP-Cryptate (diluted with pyrolysis buffer at 1:20) was added to the cell plate, and the cell plate was centrifuged at 1000 rpm for 1 minute, and incubated at room temperature without light for 1 hour.

(10) Detection: the cell plate was centrifuged at 1000 rpm for 1 minute, and the plate was read with Envision (excitation light 340 nm, emission light 620 nm and 665 nm). The ratio of two channel signals (665 nm/620 nm) multiplied by 10000 was used as the final raw data for analysis, and the $IC_{50}$ values of the compounds were calculated.

3. Experimental Results: as Shown in Table 3

TABLE 3

Test results of functional activity of compounds of the present disclosure on $D_{2L}$ and $D_{2s}$ receptors

| Number of embodiment | $D_{2L}$ $IC_{50}$ (nM) | $D_{2s}$ $IC_{50}$ (nM) |
|---|---|---|
| Embodiment 1 | 20.28 | 95.44 |
| Embodiment 1-A | 30.86 | 261.00 |
| Embodiment 1-B | 15.53 | 63.07 |
| Embodiment 3 | 51.42 | 207.10 |
| Embodiment 4 | 13.40 | 82.83 |
| Embodiment 5 | 13.11 | 93.37 |
| Embodiment 7 | 40.84 | 294.60 |
| Comparative embodiment 1 | 199.70 | 363.60 |
| Comparative embodiment 1-A | 88.77 | 264.30 |
| Comparative embodiment 2 | 35.77 | 622.40 |
| ITI-007 | 131.30 | 343.70 |

4. Experimental Conclusion

It is concluded from the above scheme that the compounds of the present disclosure have a relatively good antagonistic effect on both D2L and Des receptors.

Test Example 4: PK Test of the Compounds of the Present Disclosure on ICR Mice

1. Experimental Purpose

Male ICR mice were administered by oral gavage administration, and blood concentration of the compound of the present disclosure in mice was measured, and PK parameters were calculated, and the pharmacokinetics of the compound of the present disclosure was evaluated.

2. Experimental Materials (1) Experimental compound: compound of the embodiment of the present disclosure, self-made.

(2) Experimental animals: ICR mouse, SPF grade, male, Shanghai Slac Laboratory Animal Co., Ltd.

(3) Main experimental instruments:

| Name | Model | Manufacturer |
|---|---|---|
| Triple quadrupole liquid chromatography-mass spectrometer of AB company | Triple Quad 5500+ QTRAP | SCIEX |
| Dual range balances of Sartorius | SECURA225D-ICN | Sartorius Scientific Instruments Co., Ltd. |
| Desktop high-speed frozen centrifuge | Thermo 75009915 | Thermo Scientific |
| RAININ micropipette | 20/200/1000 μL | RAININ ® Company of USA |
| Microplate oscillator | 88882006 | Thermo Scientific |
| Desktop ultrasonic cleaning machine | KQ5200DE | Kun Shan Ultrasonic Instruments Co., Ltd |
| Vortex oscillator | Vortex genie 2 | Scientific Industries Inc of America |
| Pure water meter | Milli-Q IQ7000 | Merck of Germany |

(4) Main Experimental Reagents:

| Name | Batch number | Manufacturer |
|---|---|---|
| Acetonitrile | Chromatographic purity/204198 | Fisher chemical |
| Methanol | Chromatographic purity/203509 | Fisher chemical |
| Formic acid | A118P-500/192549 | Fisher chemical |

3. Experimental Scheme (1) Administration Information:

Preparation of drug: The test compound was taken, and physiological saline was added, and ultrasonication was performed.

Administration route and dosage: administered by oral gavage, administration dosage: 5 mg/kg, administration volume: 10 mL/kg.

Administration frequency and duration: single dose.

(2) Experimental Method:

ICR mice were stratified by body weight and then randomly grouped into 3 mice per group, and fasted overnight before the experiment. After oral gavage administration, at 0, 0.033, 0.083, 0.5, 1, 2, 4, 6 and 8 hours, 250 μL of blood was collected from the mandibular vein or saphenous vein of mice and put into sample tubes containing the anticoagulant sodium heparin, and the sample tube was placed in wet ice, centrifuged at 4 000 $r \cdot min^{-1}$ for 10 minutes, and the plasma was separated and cryopreserved in a refrigerator at −80° C. for testing.

4. Experimental Results and Analysis

The blood concentration-time data of the compound of the present disclosure measured by gavage administration were substituted into Winnonlin 8.2 program to calculate the main pharmacokinetic parameters. $T_{max}$ and $C_{max}$ were measured values, $AUC_{0-t}$ and $AUC_{0-\infty}$ values were calculated by trapezoidal method, and $t_{1/2}$ was calculated by the concentration point at the end of elimination phase via semi-logarithmic drawing method. Specific results are as shown in Table 4.

TABLE 4

| Results of pharmacokinetics test in mice | | | | | |
|---|---|---|---|---|---|
| Group | $t_{1/2}$ (h) | $C_{max}$ (ng/mL) | $T_{max}$ (h) | $AUC_{(inf)}$ (ng · h/mL) | $AUC_{(0-t)}$ (ng · h/mL) |
| Embodiment 1-A | 3.14 | 109.33 | 0.17 | 189.85 | 155.11 |
| ITI-007 | 5.00 | 13.48 | 0.28 | 59.09 | 39.33 |

5. Experimental Conclusion

From the results of the pharmacokinetic test in mice in the table, it can be seen that the compound of the present disclosure can be rapidly absorbed after administration and exhibit good metabolic properties, and the compound of the present disclosure exhibits good performance in both exposure AUC and maximum blood concentration $C_{max}$.

Test Example 5: Experiment of the Effects of the Compounds of the Present Disclosure on MK-801 Induced Hyperactivity Behavior in Mice 1. Experimental Purpose The efficacy of the compounds of the present disclosure was evaluated by high activity model of mice induced by intraperitoneal injection of MK-801.

2. Experimental Scheme (1) Experimental Materials:

Test compound: compounds of the embodiments of the present disclosure, self-made.

MK-801 (dizocilpine maleate, (+)-MK-801 hydrogen maleate), SIGMA, M107-250MG.

Solvent: pure water, Guangzhou Watsons Food & Beverage Co., Ltd., 20200928 C; physiological saline, Shandong Hualu Pharmaceutical Co., Ltd., SD20080806.

(2) Main Experimental Instruments:

| Name | Model | Manufacturer |
|---|---|---|
| Precision electronic balance | XSE105DU | METTLER TOLEDO |
| Electronic balance | TD50001 | Tianjin Tianma Hengji Instrument Co., Ltd |
| Hikvision video system | H.265 series NVR | Hangzhou Hikvision Digital Technology Co., Ltd |
| TopScan Version 3.00 (Animal Video Analysis System) | Version 3.00 | Clever Sys, Inc. |

(3) Experimental Animals:

Experimental animals: ICR mice, male, 8 mice/group, Spelford (Beijing) Biotechnology Co., Ltd.

(4) Administration Information:

Preparation of drug: the test compounds were taken, and pure water was added, and ultrasonication was performed.

Administration route and method: gavage administration, 10 mL/kg (body weight).

Administration frequency and duration: single dose.

Animals were stratified by body weight and then randomly divided into blank group, model group, and administration group, and detailed information of administration is shown in the following table.

| Group | Dosage of administration (mg/kg, i.g.) | Modeling dose of MK-801 (mg/kg, i.p.) | Number of group | Number of animals (8 animals/group, ♂) |
|---|---|---|---|---|
| Blank group | 0 | 0 | 1 | 8 |
| Model group | 0 | 0.3 | 1 | 8 |
| Embodiment 1 | 0.1, 0.3, 1 | 0.3 | 3 | 24 |
| Embodiment 1-A | 0.03, 0.1, 0.3, 1, 3 | 0.3 | 5 | 40 |
| Embodiment 7 | 0.03, 0.1, 0.3, 1, 3 | 0.3 | 5 | 40 |
| Comparative embodiment 1 | 0.3, 1, 3 | 0.3 | 3 | 24 |
| ITI-007 | 0.3, 1, 3 | 0.3 | 3 | 24 |

(5). Experimental Method:

Mice were stratified according to body weight and then randomly divided into model group, blank group and each administration group. One hour after the gavage administration of solvent or drug, 0.3 mg/kg MK-801 was injected intraperitoneally (the blank group was injected with the same volume of physiological saline), and then the mice were put into an independent activity box (a black polyethylene box with the specification of 29 cm×29 cm×30 cm) for video recording for 60 minutes, and video analysis was performed at the end of the recording to evaluate the activity of the mice.

(6) Data Processing and Statistics:

The experimental data were expressed as $\bar{x}\pm SD$, and SPSS statistical software was used to test the homogeneity of variance. If the variance was homogeneous, single factor analysis of variance was performed, and Dunnett t test is used for pairwise comparison. The $ED_{50}$ was calculated by nonlinear fitting with GraphPad Primis5 software.

3. Experimental Results: as Shown in Table 5

TABLE 5

| Experiment results of the effects of the compounds of the present disclosure on MK-801 induced hyperactivity behavior in mice | | |
|---|---|---|
| Group | $ED_{50}$ (mg/kg) | MED (mg/kg) |
| Embodiment 1 | 0.11 | 0.1 |
| Embodiment 1-A | 0.08 | 0.03 |
| Embodiment 7 | 0.09 | 0.1 |
| Comparative embodiment 1 | 1.28 | 1 |
| ITI-007 | 1.03 | 1 |

Note:
$ED_{50}$ is the half effective dose, and MED is the lowest effective dose.

4. Experimental Conclusion

It is concluded from the above scheme that the compounds of the present disclosure significantly inhibit MK-801-induced hyperactivity, and compared with the comparative embodiment, the compounds of the disclosure have lower minimum effective dose and stronger inhibitory effect.

Test Example 6: Experiment of the Effects of the Compounds of the Present Disclosure on DOI-Induced Head-Shaking Behavior in Mice 1. Experimental Purpose The efficacy of the compounds of the present disclosure was evaluated by the mice model of head-shaking behavior induced by intraperitoneal injection of (±) DOI (a hallucinogenic agent usually used to replicate anti-schizophrenic animal model).

2. Experimental Scheme (1) Experimental Materials:

Test compound: compounds of the embodiments of the present disclosure, self-made.

(±)-DOI hydrochloride, SIGMA, D101-100MG.

Solvent: pure water, Guangzhou Watsons Food & Beverage Co., Ltd., 20200928 C; physiological saline, Shandong Hualu Pharmaceutical Co., Ltd., SD20080806.

(2) Main Experimental Instruments:

| Name | Model | Manufacturer |
|---|---|---|
| Precision electronic balance | XSE105DU | METTLER TOLEDO |
| Electronic balance | TD50001 | Tianjin Tianma Hengji Instrument Co., Ltd |

(3) Experimental Animals:

Experimental animals: ICR mice, male, 8 mice/group, Spelford (Beijing) Biotechnology Co., Ltd.

(4) Administration Information:

Preparation of drug: the test compounds were taken, and solvent was added, and ultrasonication was performed.

Administration route and method: oral gavage administration, 10 mL/kg (body weight).

Administration frequency and duration: single dose.

Animals were stratified by body weight and then randomly divided into blank group, model group, and administration groups, and detailed information of administration is shown in the following table.

| Group | Dosage of administration (mg/kg, i.g.) | Modeling dose of DOI (mg/kg, i.p.) | Number of group | Number of animals (8 animals/ group, ♂) |
|---|---|---|---|---|
| Blank group | 0 | 0 | 1 | 8 |
| Model group | 0 | 1 | 1 | 8 |
| Embodiment 1-A | 0.01, 0.03, 0.1 | 1 | 3 | 24 |
| Embodiment 3 | 0.1, 0.3, 1 | 1 | 3 | 24 |
| Embodiment 4 | 0.1, 0.3, 1, 3 | 1 | 4 | 32 |

(5) Experimental Method:

Mice were stratified according to body weight and then randomly divided into model group, blank group and each administration group. One hour after the animals were gavage administration of the solvent or drugs, they were placed in a beaker (13 cm in diameter, 19 cm in height) with fresh padding, and the model drug DOI was injected intraperitoneally at a dose of 1 mg/kg. The times of head-shaking were recorded within 0-20 minutes after DOI was injected intraperitoneally.

Head-shaking behavior is defined as rapid rotational twitch of mouse's head or wet dog-like shaking, which should be different from normal hair grooming or inquiry behavior.

(6) Data Processing and Statistics:

The experimental data were expressed as $\bar{x}$±SD, and SPSS statistical software was used to test the homogeneity of variance. If the variance was homogeneous, single factor analysis of variance was performed, and Dunnett t test is used for pairwise comparison. The $ED_{50}$ was calculated by nonlinear fitting with GraphPad Primis5 software.

3. Experimental Results: as Shown in Table 6

TABLE 6

Experimental results of the effects of the compounds of the present disclosure on DOI-induced head-shaking behavior in mice

| Group | $ED_{50}$ (mg/kg) |
|---|---|
| Embodiment 1-A | 0.024 |
| Embodiment 3 | 0.21 |
| Embodiment 4 | 0.42 |

Note:
$ED_{50}$ is the half effective dose.

4. Experimental Conclusion

It is concluded from the above scheme that the compounds of the present disclosure significantly inhibit DOI-induced head-shaking behavior.

Although the embodiments of the present disclosure have been shown and described above, it is to be understood that the above embodiments are illustrative and should not be construed as limitations of the present disclosure, and those of ordinary skill in the art can make changes, modifications, substitutions and variations to the above embodiments within the scope of the present disclosure.

What is claimed is:

1. A compound represented by general formula (I), a stereoisomer thereof or a pharmaceutically acceptable salt thereof, (I)

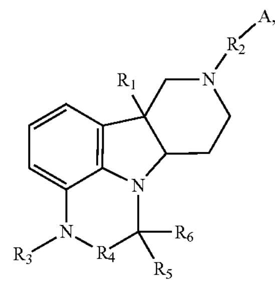

wherein, $R_1$ is independently C1-C6 alkyl;

$R_2$ is independently —$R_7$—$R_8$—$R_9$—;

$R_3$ is independently any one of hydrogen or C1-C3 alkyl;

$R_4$ is independently any one of —C(═O)— or —$CH_2$—;

$R_5$ and $R_6$ are each independently any one of hydrogen, or C1-C3 alkyl optionally substituted by halogen, C1-C3 alkoxy, cyano, amino, nitro, hydroxyl, C2-C4 alkenyl, C2-C4 alkynyl, or $R_5$, $R_6$ and the carbon atom directly attached thereto together form —C(═O)—;

$R_7$ is independently C1-C5 alkylene;

$R_8$ is independently any one of —C(═O)—, —$CH_2$— or —O—;

$R_9$ is independently any one of C1-C3 alkylene or absence;

A is phenyl optionally substituted by one or more halogens.

2. The compound represented by general formula (I), the stereoisomer thereof or the pharmaceutically acceptable salt thereof as claimed in claim 1, wherein the compound represented by general formula (I) satisfies one or more of the following conditions:

(1) the $R_1$ is independently C1-C3 alkyl;

(2) the $R_5$ and $R_6$ are each independently any one of hydrogen or unsubstituted C1-C3 alkyl, or $R_5$, $R_6$ and the carbon atom directly attached thereto together form —C(═O)—;

(3) A is independently phenyl substituted by one or more halogens;

(4) $R_4$ is —C(═O)—.

3. The compound represented by general formula (I), the stereoisomer thereof or the pharmaceutically acceptable salt thereof as claimed in claim 2, wherein the C1-C3 alkyl is selected from any one of methyl, ethyl or propyl.

4. The compound represented by general formula (I), the stereoisomer thereof or the pharmaceutically acceptable salt thereof as claimed in claim 1, wherein, the compound represented by general formula (I) is selected from a compound represented by the following general formula (I-A):

(I-A)

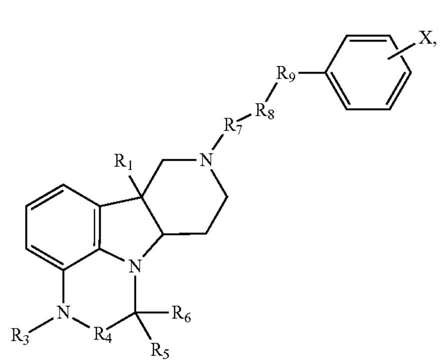

wherein,

X is halogen; any substitutable position of the benzene ring is substituted by X; the number of X is one or more;

the halogen is any one of fluorine, chlorine, bromine or iodine.

5. The compound represented by general formula (I), the stereoisomer thereof or the pharmaceutically acceptable salt thereof as claimed in claim 4, wherein, the compound represented by general formula (I) is selected from a compound represented by the following general formula (I-B):

(I-B)

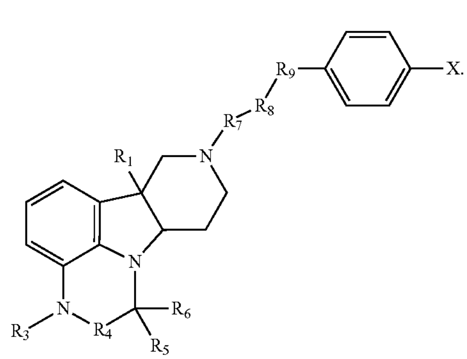

6. The compound represented by general formula (I), the stereoisomer thereof or the pharmaceutically acceptable salt thereof as claimed in claim 5, wherein, the compound represented by general formula (I) is selected from a compound represented by the following general formula (I-B):

(I-B)

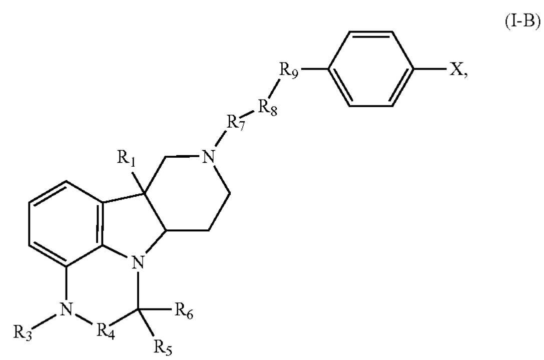

wherein, $R_1$ is independently any one of methyl, ethyl or propyl;

$R_3$ is independently any one of hydrogen, methyl, ethyl or propyl;

$R_4$ is independently any one of —C(═O)— or —$CH_2$—;

$R_5$ and $R_6$ are each independently any one of hydrogen, methyl or ethyl, or $R_5$, $R_6$ and the carbon atom directly attached thereto together form —C(═O)—;

$R_7$ is independently any one of —$CH_2$—$CH_2$—, —$CH_2$—$CH_2$—$CH_2$— or —$CH_2$—$CH_2$—$CH_2$—$CH_2$—;

$R_8$ is independently any one of —C(═O)—, —$CH_2$— or —O—;

$R_9$ is independently any one of —$CH_2$—$CH_2$—, —$CH_2$— or absence;

X is independently any one of fluorine or chlorine.

7. The compound represented by general formula (I), the stereoisomer thereof or the pharmaceutically acceptable salt thereof as claimed in claim 1, wherein, the compound represented by general formula (I) is selected from a compound represented by the following general formula (I-C):

(I-C)

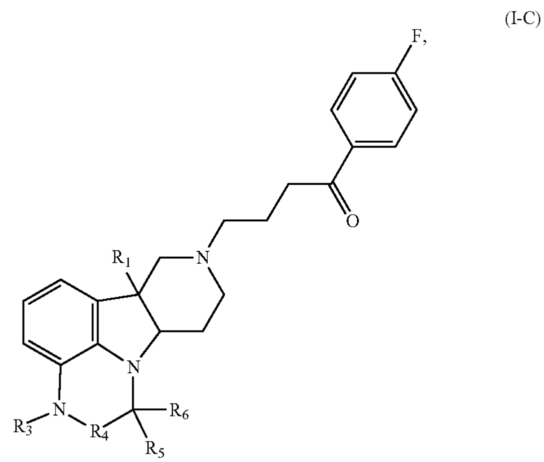

wherein, $R_1$ is independently any one of methyl, ethyl or propyl;

$R_3$ is independently any one of methyl, ethyl or propyl;

$R_4$ is independently any one of —C(═O)— or —$CH_2$—;

$R_5$ and $R_6$ are each independently any one of hydrogen, methyl or ethyl, or $R_5$, $R_6$ and the carbon atom directly attached thereto together form —C(═O)—.

8. The compound represented by general formula (I), the stereoisomer thereof or the pharmaceutically acceptable salt thereof as claimed in claim 1, wherein the compound represented by general formula (I) satisfies one or more of the following conditions:

(1) the compound represented by general formula (I) is selected from any one of the following specific compounds:

1

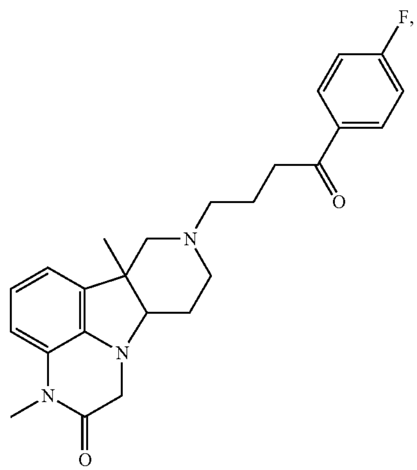

1-A

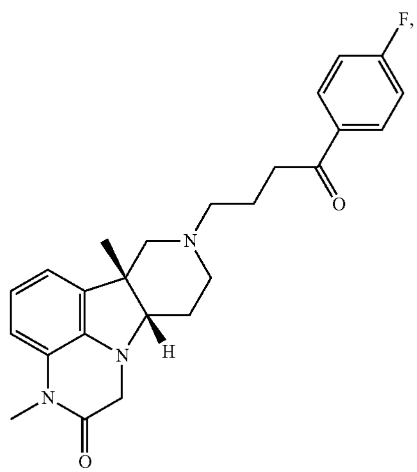

-continued

1-B

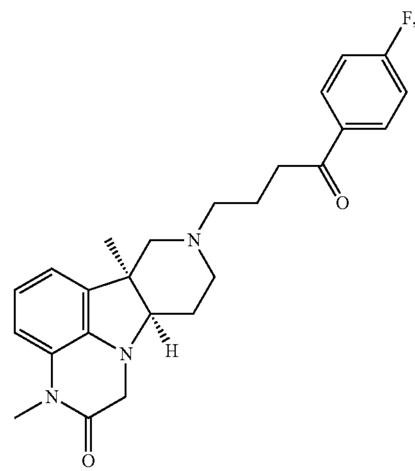

2

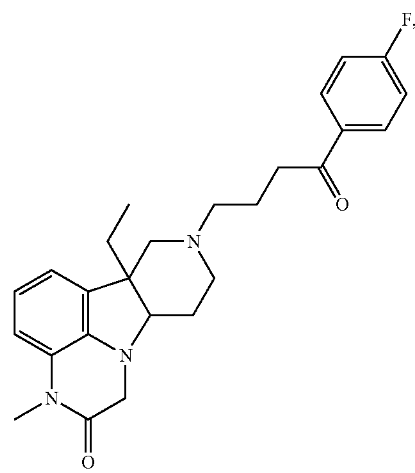

2-A

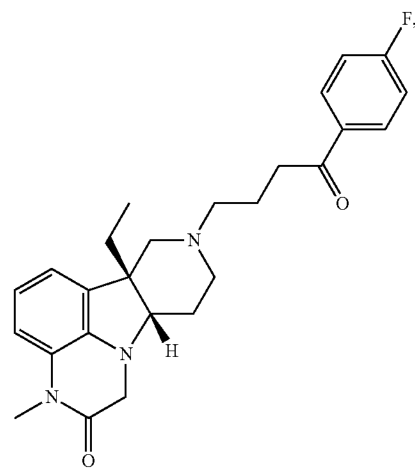

-continued
2-B
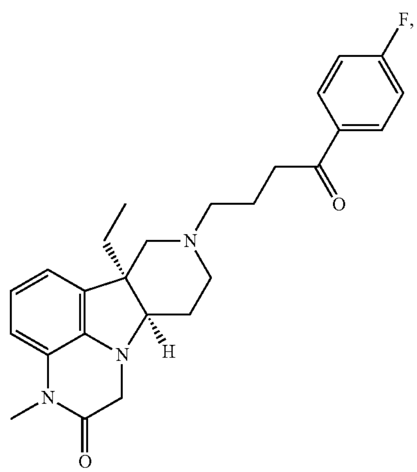
3-B
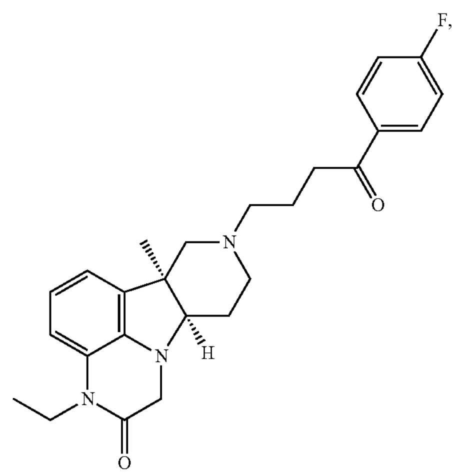
3
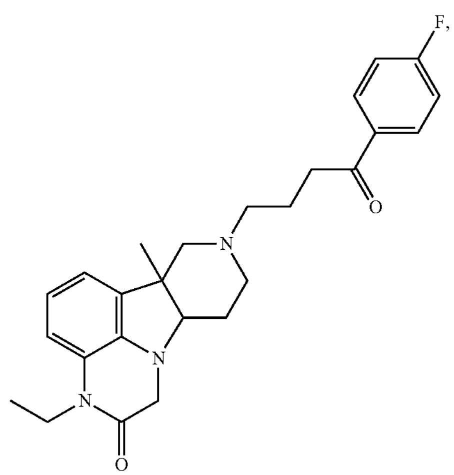
4
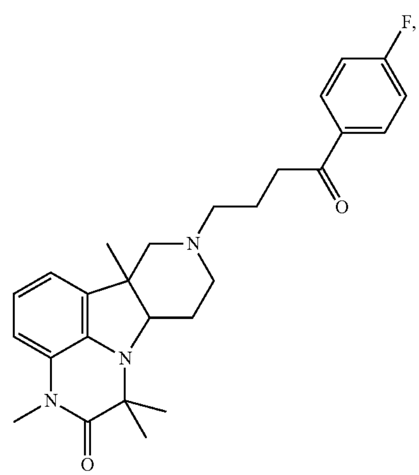
3-A
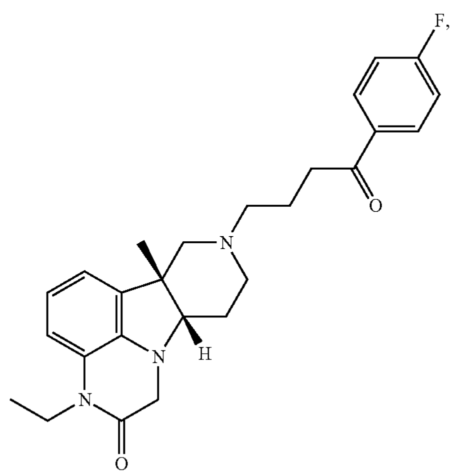
4-A
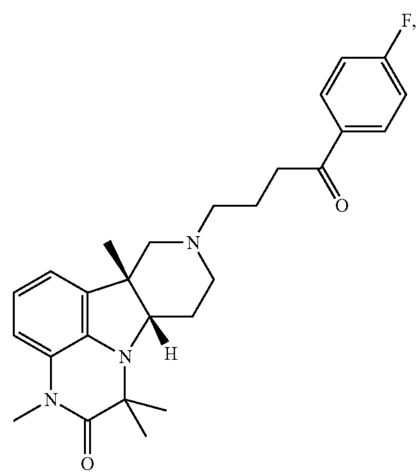

-continued
4-B
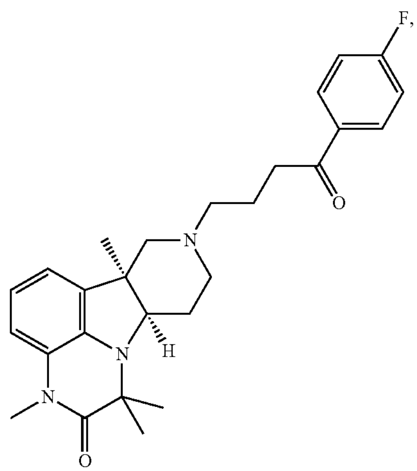
5
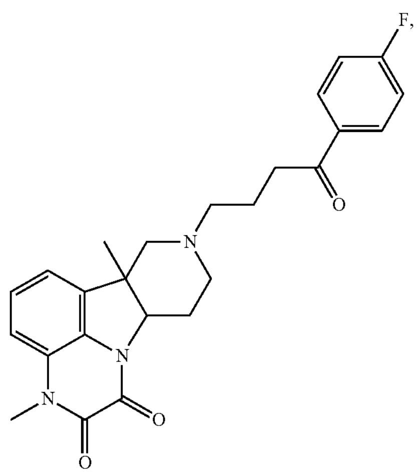
5-A
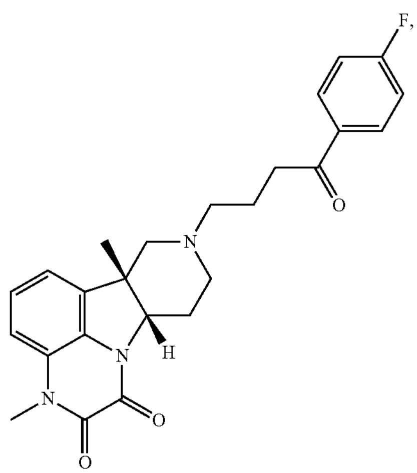
-continued
5-B
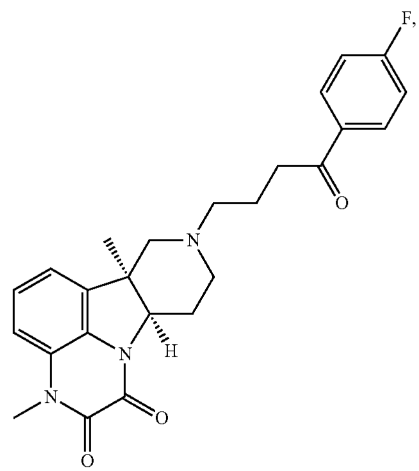
6
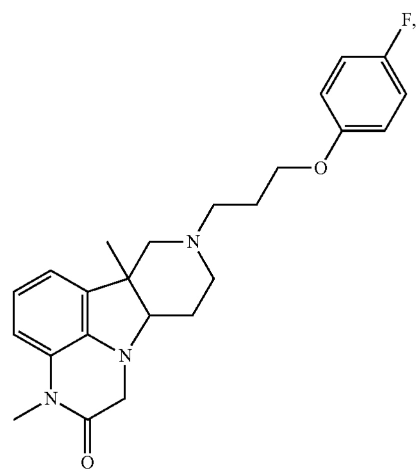
6-A
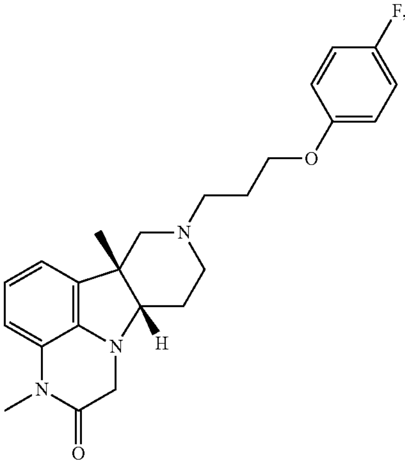

-continued

6-B

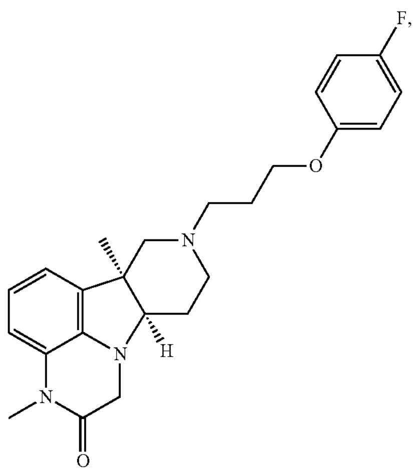

F,

7

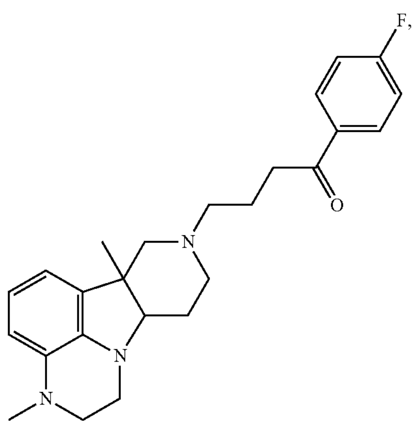

F,

7-A

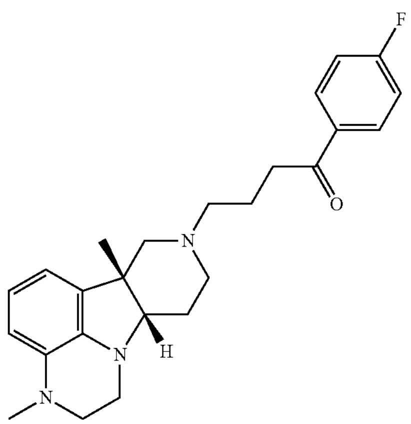

or

-continued

7-B

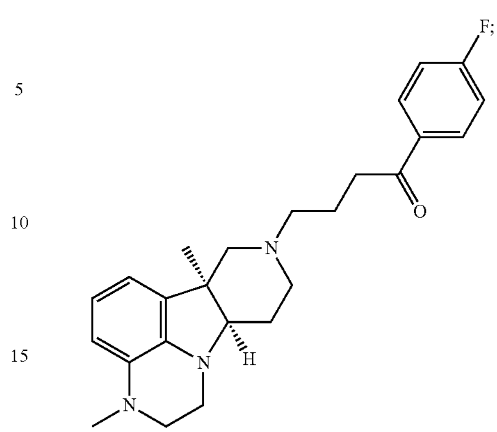

F;

(2) the pharmaceutically acceptable salt is selected from fumarate, maleate, phosphate, nitrate, sulfate, benzenesulfonate or oxalate.

9. A method for preparing the compound represented by general formula (I), the stereoisomer thereof or the pharmaceutically acceptable salt thereof as claimed in claim 1, comprising the following steps:

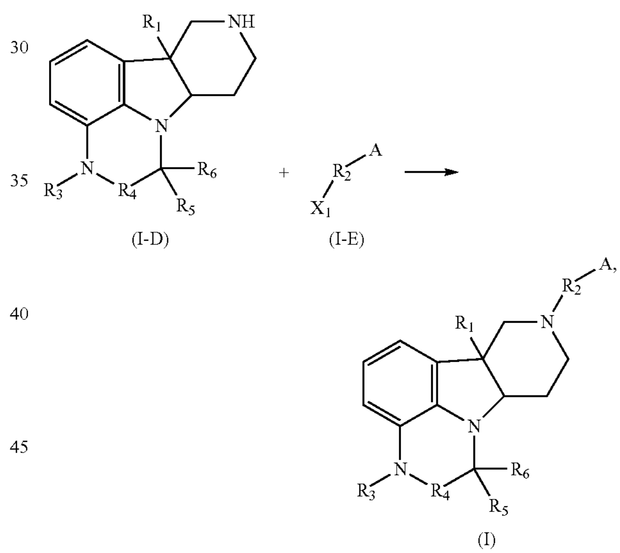

(I-D) (I-E)

(I)

preparing the compound represented by general formula (I) by a nucleophilic substitution reaction between a compound of general formula (I-D) and a compound of general formula (I-E);

wherein, $X_1$ is halogen and is selected from fluorine, chlorine, bromine or iodine.

10. A pharmaceutical composition, comprising a therapeutically effective amount of the compound represented by general formula (I), the stereoisomer thereof or the pharmaceutically acceptable salt thereof as claimed in claim 1, and a pharmaceutically acceptable carrier.

11. The method as claimed in claim 10, wherein, the depression is major depressive disorder, or, the hyperactivity disorder is attention deficit hyperactivity disorder.

12. A method of involving or regulating a 5-HT2A receptor, the serotonin transporter, a dopamine D1 receptor or a dopamine D2 receptor in a subject in need thereof, comprising administering a therapeutically effective amount of the compound represented by general formula (I), the stereoisomer thereof, or the pharmaceutically acceptable salt thereof as claimed in claim 1 to the subject wherein diseases treatable by such regulation are selected from any one or more of depression, anxiety disorder, dementia, schizophrenia, sleep disorder, dyskinesia, behavioral disorder of dementia patient, Parkinson's disease, Alzheimer's disease, migraine, hyperactivity disorder, obsessive-compulsive disorder, social phobia, neurodegenerative disease, bipolar disorder, post-traumatic stress syndrome, addictive disorder, withdrawal syndrome or attention deficit.

13. The compound represented by general formula (I), the stereoisomer thereof or the pharmaceutically acceptable salt thereof as claimed in claim 1, wherein the compound represented by general formula (I) satisfies one or more of the following conditions:

(1) the C1-C5 alkylene is selected from C3-C5 alkylene;

(2) the C1-C3 alkylene is selected from C1-C2 alkylene;

(3) C1-C3 alkyl in the optionally substituted C1-C3 alkyl is selected from any one of methyl, ethyl or propyl;

(4) the halogen is any one of fluorine, chlorine, bromine or iodine.

* * * * *